(12) United States Patent
Younes

(10) Patent No.: US 9,422,396 B2
(45) Date of Patent: Aug. 23, 2016

(54) BIODEGRADABLE ELASTOMERS PREPARED BY THE CONDENSATION OF AN ORGANIC DI-, TRI- OR TETRA-CARBOXYLIC ACID AND AN ORGANIC DIOL

(71) Applicant: Husam Younes, Doha (QA)

(72) Inventor: Husam Younes, Doha (QA)

(73) Assignee: QATAR UNIVERSITY, Doha (QA)

( * ) Notice: Subject to any disclaimer, the term of this patent is extended or adjusted under 35 U.S.C. 154(b) by 0 days.

(21) Appl. No.: 13/864,759

(22) Filed: Apr. 17, 2013

(65) Prior Publication Data

US 2013/0237625 A1 Sep. 12, 2013

Related U.S. Application Data

(62) Division of application No. 12/602,412, filed as application No. PCT/CA2008/000870 on May 8, 2008, now abandoned.

(60) Provisional application No. 60/940,441, filed on May 28, 2007, provisional application No. 61/049,389, filed on Apr. 30, 2008.

(30) Foreign Application Priority Data

May 8, 2008 (WO) ................ PCT/CA2008/000870

(51) Int. Cl.
*C08G 64/42* (2006.01)
*A61L 15/26* (2006.01)
(Continued)

(52) U.S. Cl.
CPC .............. *C08G 64/42* (2013.01); *A61L 15/26* (2013.01); *A61L 15/40* (2013.01); *A61L 15/44* (2013.01); *A61L 27/18* (2013.01); *A61L 27/3604* (2013.01); *A61L 27/383* (2013.01); *A61L 27/54* (2013.01); *A61L 27/60* (2013.01); *A61L 29/06* (2013.01); *A61L 29/16* (2013.01); *A61L 31/06* (2013.01); *A61L 31/16* (2013.01); *C08G 63/16* (2013.01); *C08G 63/20* (2013.01); *C08G 63/21* (2013.01); *C08G 63/52* (2013.01); *C08G 63/66* (2013.01);
(Continued)

(58) Field of Classification Search
None
See application file for complete search history.

(56) References Cited

U.S. PATENT DOCUMENTS

| 3,072,680 A | 1/1963 | Starcher et al. |
| 4,938,763 A | 7/1990 | Dun et al. |

(Continued)

FOREIGN PATENT DOCUMENTS

| WO | WO 2006053936 | 5/2006 |
| WO | WO 2006055940 | 5/2006 |

(Continued)

OTHER PUBLICATIONS

Borzacchiello et al, Synthesis and Characterization of Saturated and Unsaturated Poly(alkylene tartarate)s and further Crosslinking, Journal of Bioactive and Compatible Polymers vol. 15, Jan. 2000, 60-71.*

(Continued)

*Primary Examiner* — Alicia Bland
(74) *Attorney, Agent, or Firm* — Richard C. Litman

(57) ABSTRACT

The present disclosure relates to biodegradable and biocompatible elastomeric polymers that are amorphous and have a glass transition temperature below both room temperature and body temperature, and which will homogenously degrade to water soluble by-products with no reported toxicity.

21 Claims, 27 Drawing Sheets

(51) Int. Cl.
| | | |
|---|---|---|
| A61L 15/40 | (2006.01) | |
| A61L 15/44 | (2006.01) | |
| A61L 27/18 | (2006.01) | |
| A61L 27/36 | (2006.01) | |
| A61L 27/38 | (2006.01) | |
| A61L 27/54 | (2006.01) | |
| A61L 27/60 | (2006.01) | |
| A61L 29/06 | (2006.01) | |
| A61L 29/16 | (2006.01) | |
| A61L 31/06 | (2006.01) | |
| A61L 31/16 | (2006.01) | |
| C08G 63/16 | (2006.01) | |
| C08G 63/20 | (2006.01) | |
| C08G 63/21 | (2006.01) | |
| C08G 63/52 | (2006.01) | |
| C08G 63/66 | (2006.01) | |
| C08G 63/91 | (2006.01) | |
| C08J 3/24 | (2006.01) | |
| C08K 5/151 | (2006.01) | |
| A61K 9/00 | (2006.01) | |
| A61K 47/34 | (2006.01) | |

(52) U.S. Cl.
CPC .............. *C08G 63/914* (2013.01); *C08J 3/243* (2013.01); *C08K 5/151* (2013.01); *A61K 9/0024* (2013.01); *A61K 47/34* (2013.01); *A61L 2300/00* (2013.01); *C08J 2367/00* (2013.01)

(56) References Cited

U.S. PATENT DOCUMENTS

| | | | |
|---|---|---|---|
| 5,410,016 | A | 4/1995 | Hubbell et al. |
| 5,632,727 | A | 5/1997 | Tipton et al. |
| 6,004,573 | A | 12/1999 | Rathi et al. |
| 6,800,663 | B2 | 10/2004 | Asgarzadeh et al. |
| 6,984,393 | B2 | 1/2006 | Amsden |
| 7,018,645 | B1 | 3/2006 | Piao et al. |
| 7,629,003 | B2 | 12/2009 | Pisano et al. |
| 2003/0086958 | A1* | 5/2003 | Arnold ............... A61K 69/1647 424/423 |
| 2003/0105245 | A1* | 6/2003 | Amsden ................... 525/450 |
| 2004/0253203 | A1* | 12/2004 | Hossainy et al. ........ 424/78.08 |
| 2005/0063939 | A1* | 3/2005 | Ameer ................. C08G 63/06 424/78.37 |
| 2006/0057208 | A1 | 3/2006 | Holzer et al. |
| 2006/0233857 | A1 | 10/2006 | Amsden et al. |

FOREIGN PATENT DOCUMENTS

| | | |
|---|---|---|
| WO | WO 2006102530 | 9/2006 |
| WO | WO 2006118987 | 9/2006 |

OTHER PUBLICATIONS

Amsden BG, Misra G, Gu F, Younes HM .2004. Synthesis and characterization of a photo-cross-linked biodegradable elastomer. Biomacromolecules 5: 2479-2486.

Andronova N, Srivastava RK, Albertsson AC .2005. Potential tissue implants from the networks based on 1,5-dioxepan-2-one and ε-caprolactone. Polymer 46: 6746-6755.

T. Aoyagi, F. Miyata and Y Nagase. Preparation of cross-linked aliphatic polyester and application in thermo-responsive material, J.Control Release 32 (1):87-96, 1994.

Borzacchiello A, Ambrosio L, Nicolais L, Huang SJ .2000. Synthesis and characterization of saturated and unsaturated poly(alkylene tartrate)s and further cross-linking. Journal of Bioactive and Compatible Polymers 15: 60-71.

Bruin P, Veenstra GJ, Nijenhuis AJ, Pennings AJ .1988. Design and synthesis of biodegradable poly(ester-urethane) elastomer networks composed of non-toxic building blocks. Makromol Chem , Rapid Commun v 9: 589-594.

Jason A. Burdick, Laney M. Philpott, Kristi S. Anseth. Synthesis and characterization of tetrafunctional lactic acid oligomers: A potential in situ forming degradable orthopaedic biomaterial Journal of Polymer Science Part A: Polymer Chemistry 39 (5): 683-692, 2001.

K. A. Connors and K. S. Albert. Determination of hydroxy compounds by 4-dimethylaminopyridine-catalyzed acetylation. J.Pharm.Sci. 62 (5):845-846, 1973.

Decker C .2001. UV-radiation curing chemistry. Pigm Resin Tech 30: 278-286.

Gosline J, Lillie M, Carrington E, Guerette P, Ortlepp C, Savage K .2002. Elastic proteins: biological roles and mechanical properties. Philos Trans R Soc Lond B Biol Sci 357: 121-132.

Hiljanen-Vainio M, Karjalainen T, Seppala J .1996. Biodegradable lactone copolymers. I. Characterization and mechanical behavior of $\epsilon$-caprolactone and lactide copolymers. J Appl Polym Sci v 59: 1281-1288.

Hiljanen-Vainio MP, Orava PA, Seppala JV .1997. Properties of epsilon-caprolactone/DL-lactide (epsilon-CL/DL-LA) copolymers with a minor epsilon-CL content. Journal of Biomedical Materials Research 34: 39-46.

R. Hill and E. E. Walker. Polymer constitution and fiber properties J.Polym.Sci. 3:609, 1948.

Huang, S. J., Edelman, P. G., and Cameron, J. A. Crosslinkable polyesters for biomedical composites. Polymeric Materials Science and Engineering, Proceedings of the ACS Division of Polymeric Materials: Science and Engineering, vol. 53, Fall Meeting 1985. 53, 515-519. 1985. Chicago, IL, USA, ACS, Washington, DC, USA. Polymeric Materials Science and Engineering, Proceedings of the ACS Division of Polymeric Material.

Jonsson M,Johansson HO .2004. Effect of surface grafted polymers on the adsorption of different model proteins. Colloids Surf B Biointerfaces 37: 71-81.

Joziasse CAP, Veenstra H, Top MDC, Grijpma DW, Pennings AJ .1998. Rubber toughened linear and star-shaped poly(d,l-lactide-co-glycolide): Synthesis, properties and in vitro degradation. Polymer 39: 467-473.

Kim SH, Han Y-K, Kim YH, Hong SI .1992. Multifunctional initiation of lactide polymerization by stannous octoate/pentaerythritol. Makromol Chem 193: 1623-1631.

Lang M, Wong RP, Chu C-C .2002. Synthesis and structural analysis of functionalized poly (-caprolactone)-based three-arm star polymers. J Polym Sci Part A: Polym Chem 40: 1127-1141.

Leiva A, Gargallo L, Radic D .2004. Interfacial properties of poly(caprolactone) and derivatives. Journal of Macromolecular Science—Pure and Applied Chemistry 41 A: 577-583.

Matsuda T,Mizutani M. 2000. Molecular design of photocurable liquid biodegradable copolymers. 2. Synthesis of coumarin-derivatized oligo(methacrylate)s and photocuring. MACROMOLECULES 33: 791-794.

Matsuda T, Mizutani M, Arnold SC .2000. Molecular design of photocurable liquid biodegradable copolymers. 1. Synthesis and photocuring characteristics. Macromolecules 33: 795-800.

H. Miyasako, K. Yamamoto, A. Nakao, and T. Aoyagi. Preparation of cross-linked poly[(epsilon-caprolactone)-co-lactide] and biocompatibility studies for tissue engineering materials. Macromol. Biosci. 7 (1):76-83, 2007.

Nijenhuis AJ, Grijpma DW, Pennings AJ .1996. Crosslinked poly(L-lactide) and poly(ε-caprolactone). Polymer 37: 2783-2791.

Satulovsky J, Carignano MA, Szleifer I .2000. Kinetic and thermodynamic control of protein adsorption. Proc Natl Acad Sci U S A 97: 9037-9041.

Schindler A, Hibionada YM Pitt CG .1982. Aliphatic Polyesters. III. Molecular Weight and Molecular Weight Distribution in Alcohol-Initiated Polymerizations of epsilon-Caprolactone. Journal of Polymer Science: Polymer Chemistry Edition 20: 319-326.

Schindler, A. and Pitt, C. G. Biodegradable Elastomeric Polyesters. Polymer Preprints, Division of Polymer Chemistry, American Chemical Society: Papers Presented at the Kansas City Meeting. 23[2], 111-112. 1982. Kansas City, MO, USA, ACS, Div of Polym Chem, Washington, DC, USA. Polymer Preprints, Division of Polymer Chemistry, American Chemical Society.

(56) References Cited

OTHER PUBLICATIONS

Schliecker G, Schmidt C, Fuchs S, Kissel T .2004. Characterization and in vitro degradation of poly(2,3-(1,4-diethyl tartrate)-co-2,3-isopropyliden tartrate). J Control Release 98: 11-23.

Storey RF,Hickey TP .1994. Degradable polyurethane networks based on D,L-lactide, glycolide, epsilon -caprolactone, and trimethylene carbonate homopolyester and copolyester triols. Polymer v 35: 830-838.

Storey RF, Warren SC, Allison CJ, Puckett AD .1997. Methacrylate-encapped poly(d,l-lactide-co-trimethylene carbonate) oligomers. Network formation by thermal free-radical curing. Polymer 38: 6295-6301.

Wang Y, Ameer GA, Sheppard BJ, Langer R .2002. A tough biodegradable elastomer. Nat Biotechnol 20: 602-606.

Webb, A., Yang, J., and Ameer, G. A novel elastomer for small diameter blood vessel tissue engineering. Transactions—7th World Biomaterials Congress, May 17-21, 2004. 1674. 2004. Sydney, Australia, Biomaterials 2004 Congress Managers, Sydney, NSW 2001, Australia. Transactions—7th World Biomaterials Congress.

Wildemore JK,Jones DH .2006. Persistent Granulomatous Inflammatory Response Induced by Injectable Poly-l-lactic Acid for HIV Lipoatrophy. Dermatologic Surgery 32: 1407-1409.

Younes HM, Bravo-Grimaldo E, Amsden BG .2004. Synthesis, characterization and in vitro degradation of a biodegradable elastomer. Biomaterials 25: 5261-5269.

Younes, H. M. 2003. New biodegradable elastomers for interferon-gamma delivery. University of Alberta. Doctorate Thesis.

Zegzula HD, Buck DC, Brekke J, Wozney JM, Hollinger JO .1997. Bone formation with use of rhBMP-2 (recombinant human bone morphogenetic protein-2). J Bone Joint Surg Am 79: 1778-1790.

* cited by examiner (a)

(b)

(a)

(b)

(a)

(b)

(c)

(A) PHT (B) POT (C) PDT (D) PDDT (E) Poly styrene plate (control).

BIODEGRADABLE ELASTOMERS PREPARED BY THE CONDENSATION OF AN ORGANIC DI-, TRI- OR TETRA-CARBOXYLIC ACID AND AN ORGANIC DIOL

CROSS-REFERENCE TO RELATED APPLICATIONS

This application is a divisional application of U.S. Ser. No. 12/602,412 filed Mar. 31, 2010, which is a national stage application of PCT/CA2008/000870 filed on May 8, 2008 which claims priority from U.S. provisional application 60/940,441 filed on May 28, 2007 and U.S. provisional application 61/049,389 filed on Apr. 30, 2008, of which are incorporated herein by reference in their entirety.

FIELD OF THE DISCLOSURE

The present disclosure relates to biodegradable and biocompatible poly (alkylene carboxylate) thermoset based elastomeric materials that are prepared using either thermal crosslinking or photocrosslinking techniques.

BACKGROUND OF THE DISCLOSURE

Biodegradable elastomeric polymers have recently attracted much attention in the fields of tissue engineering and implantable drug delivery systems. The elastomeric properties of those polymeric substrates offer many advantages over the rigid and tough polymers. First, elastomeric polymers can be designed to offer resemblance to many of the mechanical characteristics and functions of the body tissues and membranes. Second, they have the ability to recover the mechanical challenges which they are subjected to when implanted in a non-static part of the body. Third, this ability to withstand the deformations and mechanical stress would help in retaining the integrity and the functionality of the implantable device. Fourth, biodegradable elastomers are well suited also in soft tissue engineering, where cells are grown into porous scaffolds (with mechanical stimulation) to generate functional tissues. Finally, elastomeric polymers have the ability to transfer mechanical signals between tissues in the place of their implantation.

Biodegradable elastomers reported in the literature have been synthesized as one of two types: thermoplastic[1-3] or thermoset elastomers[4-6]. Thermoplastics have the advantage of being easily processed by melt processing. However, the crystalline crosslinked hard regions these materials possess provide regions of much slower and heterogenous degradation, with the amorphous regions degrading faster than the crystalline segments and so produce a material with physical and mechanical properties that degrade with time in a non-linear fashion. This heterogenous degradation is undesirable for biomedical uses particularly in the drug delivery applications. On the other hand, although thermoset polymers are not easily fabricated by heat, they outperform thermoplastics in a number of areas, including uniform biodegradation, mechanical properties, chemical resistance, thermal stability, and overall durability. For all the above reasons, thermosets attracted attention for their advantageous properties.

One of the common approaches reported earlier to prepare thermoset elastomers is to first prepare multi-arm star condensation polymers by subjecting biodegradable monomers to ring opening polymerization in the presence of polyols as initiators. Some of the most common biodegradable monomers used in that approach include lactides, ε-caprolactone, glycolides, δ-valerolactone, urethane, para-dioxanone, dioexepanone and trimethylene carbonate. The most commonly used polyol initiators included glycerol, laurylalcohol, pentaerythritol and inositol.[2,6-10] The prepared star shaped condensation polymers are then crosslinked using thermal or non-thermal approaches. Some of the thermal crosslinking approaches reported involved the preparation of polyurethanes that contain the 4,4'-methylphenidate diisocyanate which degrades to toxic and carcinogenic products and raises issues of biocompatibility.[4,11] Other elastomers were prepared by thermal free-radical curing of terminal methacrylated oligomers which involved the use of incompatible catalysts and solvents.[5] Some of the compatibility issues of crosslinkers used were overcome by using bis-lactone crosslinkers.[12] These crosslinking agents were previously reported in crosslinking lactides, caprolactone and dioxepanone monomers[13-15] and lately in crosslinking star polymers made of ε-caprolactone and dl-lactide using glycerol as initiator.[6,16]

Although the elastomers made of ε-caprolactone and dl-lactide polymers can be described as absorbable, the rate of their bio-absorption is so slow that it renders the polymers practically useless for many biomedical applications. This is because the main component of the elastomers, which is polylactide absorbs very slowly in bodily tissue. The other primary component is polycaprolactone which absorbs even slower due to its high crystallinity. In addition, lactide polymerizes much faster than caprolactone at 120° C. and so, when the polymers are made, a segmented copolymer containing long segments of polylactide spaced between segments of polycaprolactone is produced. The segmented structures of the polymers further lowers its bioabsorption rate.[16]

One other disadvantage is that polymers prepared from ε-caprolactone and lactides will only be composed of hydrophobic segments that contribute to their long and slow bioabsorption and decreases biocompatibility. It is known that highly hydrophobic polymer surfaces have very high contact angles with water and therefore, they are more susceptible to protein adsorption.[17-19] This eventually results in formation of fibrous tissues around the implanted device and provokes accumulation of macrophages and other innate immune components around the implant which will eventually result in the device failure. Fibrous capsule formation and mild to severe inflammatory reactions in some cases were also reported.[20,21] On the other hand, the acrylated UV crosslinked version of the same reported polymers involved the use of organic solvents like tetrahydrofuran and dichloromethane to incorporate the drug into the precrosslinked mass. This issue raises the flag with regard to compatibility and even stability of loaded bioactive agents.[22] Finally, the preparation steps involved in preparing the above elastomers requires higher heat and it takes at least 3 days to obtain the final preparation.[6,23,24]

Another approach to prepare elastomeric polymers was also reported through polycondensation reactions between di and tri carboxylic acids and diols which were further subjected to thermal crosslinking. Elastomers based on citric acid, tartaric acid, sebacic acid monomers were reported earlier.[25-29] These elastomers either required long curing times ranging from a few days to weeks with inconsistency in the final physical and mechanical properties or the elastomers prepared were tough and brittle. In addition, high crosslinking temperatures were needed for their crosslinking which restricted their use in drug delivery of thermally sensitive therapeutic agents and other heat sensitive drugs.

There remains a need for biodegradable and biocompatible elastomeric polymers.

SUMMARY OF THE DISCLOSURE

Herein, biodegradable and biocompatible elastomer polymers that are amorphous and have a glass transition temperature below both room temperature and body temperature, and which will homogenously degrade to water soluble by-products with no reported toxicity are disclosed.

Accordingly, in one embodiment, the present disclosure includes a polymer comprising, a copolymer, the copolymer comprising polymerizing units of:

a) about 1 to about 99% by weight of, based on the total mass of the copolymer, at least one of a monomer of the formula I, II, III or IV

(I)

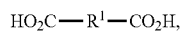
(II)

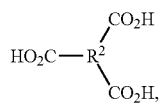
(III)

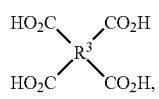
(IV)

in which $R^1$, $R^2$ and $R^3$ are independently $C_3$-$C_{20}$cycloalkylene, $C_1$-$C_{30}$alkylene, $C_2$-$C_{30}$alkenylene, or $C_2$-$C_{30}$alkynylene, said latter 3 groups being straight-chained or branched and/or interrupted by one, two or three $C_3$-$C_{10}$ cyclic moieties therein, and said 4 groups being optionally substituted by one or more groups selected from OH, halo, $OR^4$ or $R^4$, in which $R^4$ is selected from $C_1$-$C_6$alkyl, $C_2$-$C_6$alkenyl, $C_2$-$C_6$alkynyl or $C_3$-$C_6$cycloalkyl;

b) about 1 to about 99%, by weight, based on the total mass of the copolymer, of a monomer of the formula V,

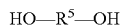
(V)

in which the radical $R^5$ is $C_3$-$C_{20}$cycloalkylene, $C_1$-$C_{30}$alkylene, $C_2$-$C_{30}$alkenylene, $C_2$-$C_{30}$alkynylene, said latter 3 groups being straight-chained or branched and/or interrupted by one, two or three $C_3$-$C_{10}$ cyclic moieties therein, wherein one or more of the carbon atoms may be replaced by oxygen, and said 4 groups being optionally substituted by one or more groups selected from OH, halo, $OR^4$ or $R^4$, in which $R^4$ is selected from $C_1$-$C_6$alkyl, $C_2$-$C_6$alkenyl, $C_2$-$C_6$alkynyl or $C_3$-$C_6$cycloalkyl;

or $R^5$ is a polyalkylene glycol or a poly-ε-caprolactone;

and wherein the copolymer is crosslinked with c) about 0.5 to about 75% by weight of the total polymer, of a crosslinker of the formula VI or VII

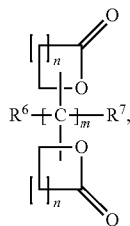
(VI)

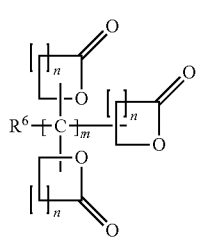
(VII)

wherein $R^6$ and $R^7$ are independently OH, halo, $OR^4$ or $R^4$, in which $R^4$ is selected from $C_1$-$C_6$alkyl, $C_2$-$C_6$alkenyl, $C_2$-$C_6$alkynyl or $C_3$-$C_6$cycloalkyl;

n is an integer from 1 to 20; and m is an integer from 0 to 20, and wherein any of the lactone rings are optionally substituted by one or more substituents selected from OH, halo, $OR^4$ or $R^4$, in which $R^4$ is selected from $C_1$-$C_6$alkyl, $C_2$-$C_6$alkenyl, $C_2$-$C_6$alkynyl or $C_3$-$C_6$cycloalkyl.

In another embodiment of the present disclosure there is disclosed a polymer comprising a copolymer, the copolymer comprising polymerizing units of:

a) about 1 to about 99% by weight of, based on the total mass of the copolymer, at least one of a monomer of the formula I, II, III or IV

(I)

(II)

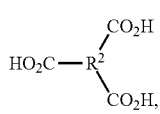
(III)

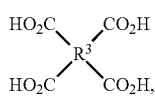
(IV)

in which $R^1$, $R^2$ and $R^3$ are independently $C_3$-$C_{20}$cycloalkylene, $C_1$-$C_{30}$alkylene, $C_2$-$C_{30}$alkenylene, or $C_2$-$C_{30}$alkynylene, said latter 3 groups being straight-chained or branched and/or interrupted by one, two or three $C_3$-$C_{10}$ cyclic moieties therein, and said 4 groups being optionally substituted by one or more groups selected from OH, halo, $OR^4$ or $R^4$, in which $R^4$ is selected from $C_1$-$C_6$alkyl, $C_2$-$C_6$alkenyl, $C_2$-$C_6$alkynyl or $C_3$-$C_6$cycloalkyl;

b) about 1 to about 99%, by weight, based on the total mass of the copolymer, of a monomer of the formula V,

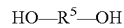
(V)

in which the radical $R^5$ is $C_3$-$C_{20}$cycloalkylene, $C_1$-$C_{30}$alkylene, $C_2$-$C_{30}$alkenylene, $C_2$-$C_{30}$alkynylene, said latter 3 groups being straight-chained or branched and/or interrupted by one, two or three $C_3$-$C_{10}$ cyclic moieties therein, wherein one or more of the carbon atoms may be replaced by oxygen, and said 4 groups being optionally substituted by one or more groups selected from OH, halo, $OR^4$ or $R^4$, in which $R^4$ is selected from $C_1$-$C_6$alkyl, $C_2$-$C_6$alkenyl, $C_2$-$C_6$alkynyl or $C_3$-$C_6$cycloalkyl;

or $R^5$ is a polyalkylene glycol or a poly-ϵ-caprolactone;

and wherein free hydroxyl groups or carboxyl groups of the copolymer are derivatized with a photosensitive compound and are photochemically crosslinked.

In an embodiment, the polymers of the present disclosure are optionally biodegradable, biocompatible and elastomeric.

The present disclosure also includes a biodegradable and biocompatible elastomeric polymer comprising a condensation polymer of an organic di-, tri- or tetra-carboxylic acid and an organic diol, said condensation polymer being either (a) thermally crosslinked with a bis- or tri-lactone; or (b) reacted with a photosensitive compound to form a photosensitive condensation polymer which is photocrosslinked, to provide the biodegradable and biocompatible elastomeric polymer.

In another embodiment of the present disclosure, methods of preparing a thermally crosslinked and photocrosslinked biodegradable and biocompatible elastomeric polymer are disclosed.

The present disclosure also includes uses of the elastomeric polymers, for example as in scaffolds for soft tissue engineering, coatings on metallic biomedical devices like catheters, needles and stents, and for implantable drug delivery systems.

Other features and advantages of the present disclosure will become apparent from the following detailed description. It should be understood, however, that the detailed description and the specific examples while indicating preferred embodiments of the disclosure are given by way of illustration only, since various changes and modifications within the spirit and scope of the disclosure will become apparent to those skilled in the art from this detailed description.

BRIEF DESCRIPTION OF THE DRAWINGS

Embodiments of the invention will be described in relation to the drawings in which.

DETAILED DESCRIPTION OF THE INVENTION

(I) Definitions

Figure 1:
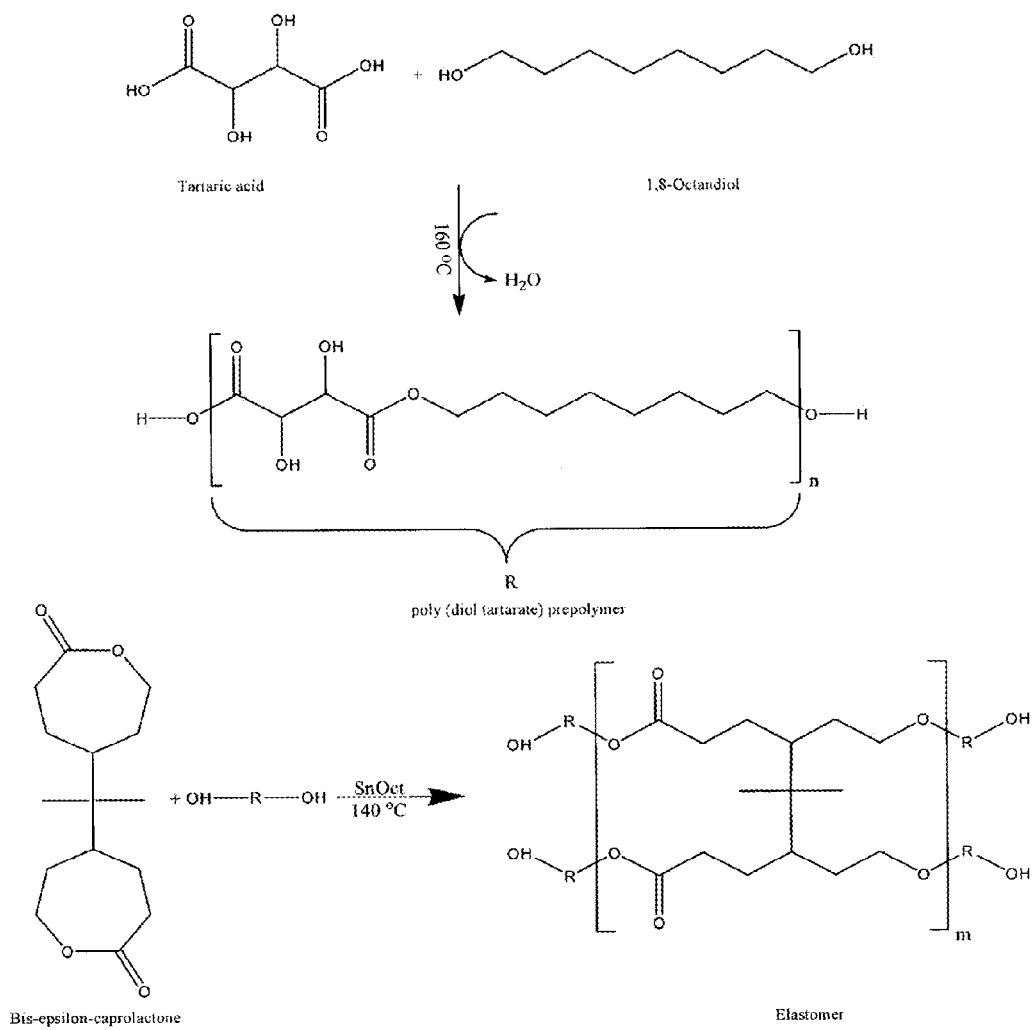
FIG. 1 shows the preparation of a biodegradable and biocompatible elastomeric polymer using tartaric acid and 1,8-octanediol (POT) to form the condensation polymer and thermally crosslinked with bis-ϵ-caprolactone according to an embodiment of the disclosure.

The term "$C_{1-n}$alkyl" as used herein means straight and/or branched chain, saturated alkyl radicals containing from one to "n" carbon atoms and includes (depending on the identity of n) methyl, ethyl, propyl, isopropyl, n-butyl, s-butyl, isobutyl, t-butyl, 2,2-dimethylbutyl, n-pentyl, 2-methylpentyl, 3-methylpentyl, 4-methylpentyl, n-hexyl and the like, where the variable n is an integer representing the largest number of carbon atoms in the alkyl radical.

The term "$C_{2-n}$alkenyl" as used herein means straight and/or branched chain, unsaturated alkyl radicals containing from two to n carbon atoms and one or more, suitably one to three, double bonds, and includes (depending on the identity of n) vinyl, allyl, 2-methylprop-1-enyl, but-1-enyl, but-2-enyl, but-3-enyl, 2-methylbut-1-enyl, 2-methylpent-1-enyl, 4-methylpent-1-enyl, 4-methylpent-2-enyl, 2-methylpent-2-enyl, 4-methylpenta-1,3-dienyl, hexen-1-yl and the like, where the variable n is an integer representing the largest number of carbon atoms in the alkenyl radical.

The term "$C_{2-n}$alkynyl" as used herein means straight and/or branched chain, unsaturated alkyl groups containing from one to n carbon atoms and one or more, suitably one to three, triple bonds, and includes (depending on the identity of n) ethynyl, 1-propynyl, 2-propynyl, 2-methylprop-1-ynyl, 1-butynyl, 2-butynyl, 3-butynyl, 1,3-butadiynyl, 3-methylbut-1-ynyl, 4-methylbut-ynyl, 4-methylbut-2-ynyl, 2-methylbut-1-ynyl, 1-pentynyl, 2-pentynyl, 3-pentynyl, 4-pentynyl, 1,3-pentadiynyl, 1,4-pentadiynyl, 3-methylpent-1-ynyl, 4-methylpent-2-ynyl-4-methylpent-2-ynyl, 1-hexynyl and the like, where the variable n is an integer representing the largest number of carbon atoms in the alkynyl radical.

The term "$C_{3-n}$cycloalkyl" as used herein means a monocyclic or polycyclic saturated carbocylic group containing from three to twenty carbon atoms and includes (depending on the identity of n) cyclopropyl, cyclobutyl, cyclopentyl, cyclodecyl, bicyclo[2.2.2]octane, bicyclo[3.1.1]heptane and the like where the variable n is an integer representing the largest number of carbon atoms in the alkynyl radical.

The phrase "interrupted by one, two or three $C_3$-$C_{10}$ cyclic moieties" as used herein means an alkylene, alkenylene or alkynylene that is interrupted by a $C_3$-$C_{10}$ cyclic alkylene moiety and includes 1,2,-dimethylene-cyclohexylene, 1,2,3-trimethylene-cyclohexylene, 1,2,3,4-tetramethylene-cyclohexylene, 1-ethylene-2,3-dimethylene-cyclohexylene, 1,2,-dimethylene-cyclopentylene, 1,2,3-trimethylene-cyclopentylene, 1,2-diethylene-cyclobutylene, 1-butylene-3-(3-(4-propylenecyclohexylene)propyl)-cyclohexylene and the like.

The term "halo" as used herein means halogen and includes chlorine, bromine, iodine and fluorine.

The suffix "ene" added on to any of the above groups means that the group is divalent, i.e. inserted between two other groups.

(II) Polymers of the Disclosure

In an embodiment of the present disclosure there is provided, a biodegradable and biocompatible elastomeric polymer comprising a condensation polymer of an organic di, tri- or tetra-carboxylic acid and an organic diol, said condensation polymer being thermally crosslinked or photocrosslinked.

Accordingly, the present disclosure includes a polymer comprising a copolymer, the copolymer comprising polymerizing units of:

a) about 1 to about 99% by weight of, based on the total mass of the copolymer, at least one of a monomer of the formula I, II, III or IV $$HO_2C-CO_2H, \quad (I)$$

$$HO_2C-R^1-CO_2H, \quad (II)$$

$$HO_2C-R^2\begin{array}{c}CO_2H\\ \diagdown\\ CO_2H,\end{array} \quad (III)$$

$$\begin{array}{c}HO_2C\\ \diagdown\\ HO_2C\end{array}R^3\begin{array}{c}CO_2H\\ \diagup\\ CO_2H,\end{array} \quad (IV)$$

in which $R^1$, $R^2$ and $R^3$ are independently $C_3$-$C_{20}$cycloalkylene, $C_1$-$C_{30}$alkylene, $C_2$-$C_{30}$alkenylene, or $C_2$-$C_{30}$alkynylene, said latter 3 groups being straight-chained or branched and/or interrupted by one, two or three $C_3$-$C_{10}$ cyclic moieties therein, and said 4 groups being optionally substituted by one or more groups selected from OH, halo, $OR^4$ or $R^4$, in which $R^4$ is selected from $C_1$-$C_6$alkyl, $C_2$-$C_6$alkenyl, $C_2$-$C_6$alkynyl or $C_3$-$C_6$cycloalkyl;

b) about 1 to about 99%, by weight, based on the total mass of the copolymer, of a monomer of the formula V, $$HO-R^5-OH \quad (V)$$

in which the radical $R^5$ is $C_3$-$C_{20}$cycloalkylene, $C_1$-$C_{30}$alkylene, $C_2$-$C_{30}$alkenylene, $C_2$-$C_{30}$alkynylene, said latter 3 groups being straight-chained or branched and/or interrupted by one, two or three $C_3$-$C_{10}$ cyclic moieties therein, wherein one or more of the carbon atoms may be replaced by oxygen, and said 4 groups being optionally substituted by one or more groups selected from OH, halo, $OR^4$ or $R^4$, in which $R^4$ is selected from $C_1$-$C_6$alkyl, $C_2$-$C_6$alkenyl, $C_2$-$C_6$alkynyl or $C_3$-$C_6$cycloalkyl;

or $R^5$ is a polyalkylene glycol or a poly-ε-caprolactone;

and wherein the copolymer is crosslinked with c) about 0.5 to about 75% by weight of the total polymer, of a crosslinker of the formula VI or VII

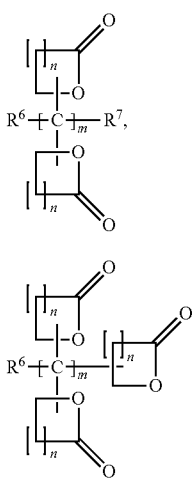

wherein $R^6$ and $R^7$ are independently OH, halo, $OR^4$ or $R^4$, in which $R^4$ is selected from $C_1$-$C_6$alkyl, $C_2$-$C_6$alkenyl, $C_2$-$C_6$alkynyl or $C_3$-$C_6$cycloalkyl;

n is an integer from 1 to 20; and m is an integer from 0 to 20, and wherein any of the lactone rings are optionally substituted by one or more substituents selected from OH, halo, $OR^4$ or $R^4$, in which $R^4$ is selected from $C_1$-$C_6$alkyl, $C_2$-$C_6$alkenyl, $C_2$-$C_6$alkynyl or $C_3$-$C_6$cycloalkyl.

The present disclosure also includes a polymer comprising a copolymer, the copolymer comprising polymerizing units of:

a) about 1 to about 99% by weight of, based on the total mass of the copolymer, at least one of a monomer of the formula I, II, III or IV

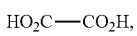  (I)

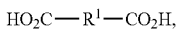  (II)

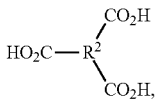  (III)

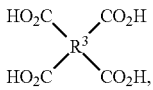  (IV)

in which $R^1$, $R^2$ and $R^3$ are independently $C_3$-$C_{20}$cycloalkylene, $C_1$-$C_{30}$alkylene, $C_2$-$C_{30}$alkenylene, or $C_2$-$C_{30}$alkynylene, said latter 3 groups being straight-chained or branched and/or interrupted by one, two or three $C_3$-$C_{10}$ cyclic moieties therein, and said 4 groups being optionally substituted by one or more groups selected from OH, halo, $OR^4$ or $R^4$, in which $R^4$ is selected from $C_1$-$C_6$alkyl, $C_2$-$C_6$alkenyl, $C_2$-$C_6$alkynyl or $C_3$-$C_6$cycloalkyl;

b) about 1 to about 99%, by weight, based on the total mass of the copolymer, of a monomer of the formula V,

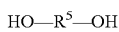  (V)

in which the radical $R^5$ is $C_3$-$C_{20}$cycloalkylene, $C_1$-$C_{30}$alkylene, $C_2$-$C_{30}$alkenylene, $C_2$-$C_{30}$alkynylene, said latter 3 groups being straight-chained or branched and/or interrupted by one, two or three $C_3$-$C_{10}$ cyclic moieties therein, wherein one or more of the carbon atoms may be replaced by oxygen, and said 4 groups being optionally substituted by one or more groups selected from OH, halo, $OR^4$ or $R^4$, in which $R^4$ is selected from $C_1$-$C_6$alkyl, $C_2$-$C_6$alkenyl, $C_2$-$C_6$alkynyl or $C_3$-$C_6$cycloalkyl;

or $R^5$ is a polyalkylene glycol or a poly-ε-caprolactone; and wherein free hydroxyl groups or carboxyl groups of the copolymer are derivatized with a photosensitive compound and are photochemically crosslinked.

In an embodiment of the disclosure, the monomers of the formula I, II, III or IV are present from: about 5% to about 95%, about 10% to about 90%, about 20% to about 80%, about 25% to about 75%, about 40% to about 60% by weight, based on the total mass of the copolymer. In another embodiment, monomers of the formula I, II, III or IV are present in at least 1%, 5%, 10%, 20%, 25%, 40%, 50%, 60%, 75%, 80%, 90%, 95%, 99%, by weight, based on the total mass of the copolymer.

In another embodiment, the monomer of the formula V is present from about 5% to about 95%, about 10% to about 90%, about 20% to about 80%, about 25% to about 75%, about 40% to about 60% by weight, based on the total mass of the copolymer. In another embodiment, the monomer of the formula V is present in at least 1%, 5%, 10%, 20%, 25%, 40%, 50%, 60%, 75%, 80%, 90%, 95%, 99%, by weight, based on the total mass of the copolymer.

In a further embodiment, the monomers of the formula VI or VII are present from about 1% to about 75%, about 5% to about 60%, about 10% to about 50%, about 20% to about 30%, by weight, based on the total mass of the polymer. In another embodiment, the monomers of the formula VI or VII are present in at least 0.5%, 1%, 5%, 10%, 20%, 25%, 30%, 40%, 50%, 60% by weight, based on the total mass of the polymer.

In another embodiment of the present disclosure, $R^1$, $R^2$ and $R^3$ are independently $C_3$-$C_{10}$cycloalkylene, $C_1$-$C_{10}$alkylene, $C_2$-$C_{10}$alkenylene, or $C_2$-$C_{10}$alkynylene, said latter 3 groups being straight-chained or branched and/or interrupted by one, two or three $C_3$-$C_6$ cyclic moieties therein, and said 4 groups being optionally substituted by one to six groups selected from OH, halo, $OR^4$ or $R^4$, in which $R^4$ is selected from $C_1$-$C_6$alkyl, $C_2$-$C_6$alkenyl, $C_2$-$C_6$alkynyl or $C_3$-$C_6$cycloalkyl. In another embodiment of the present disclosure, the monomer of formula I, II, III or IV is selected from

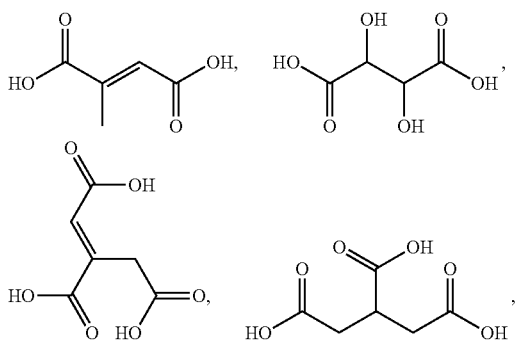

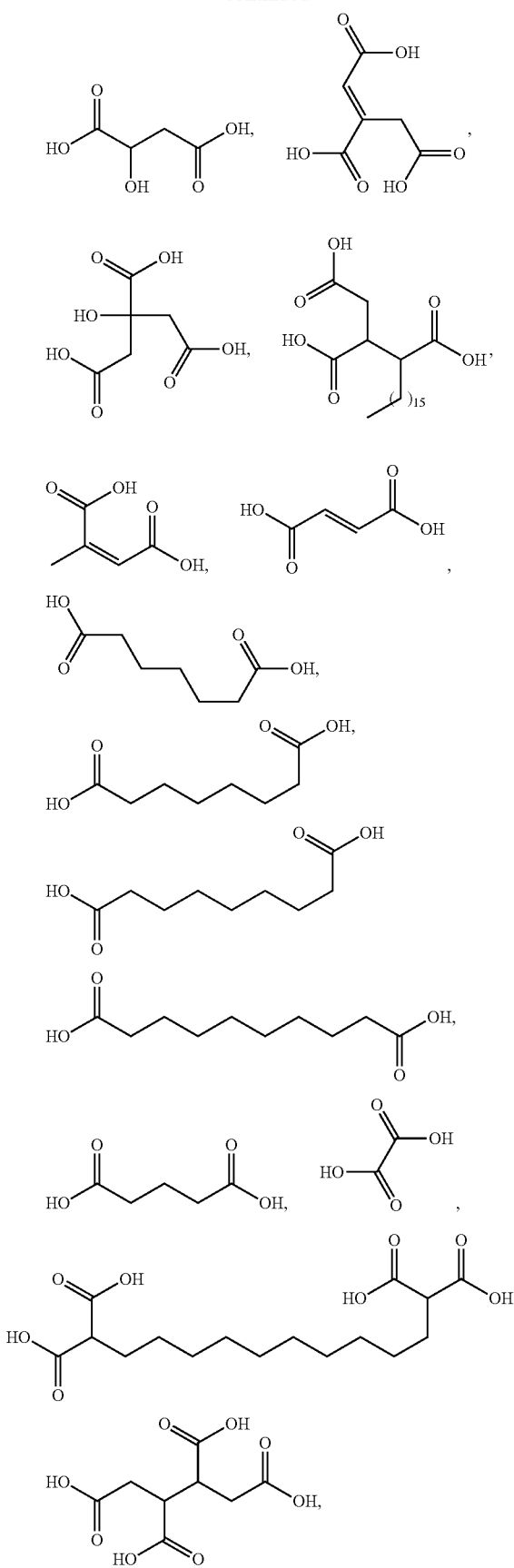

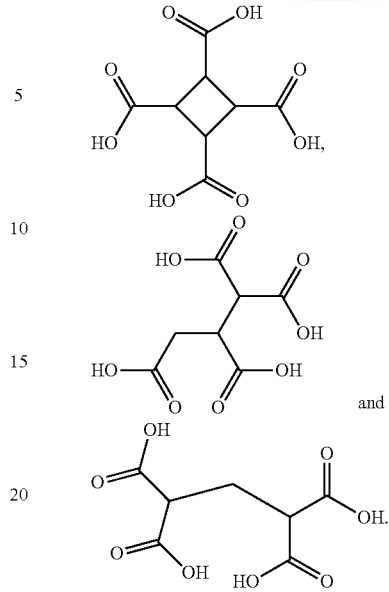

and

In a further embodiment, the monomer of formula I, II, III or IV is selected from

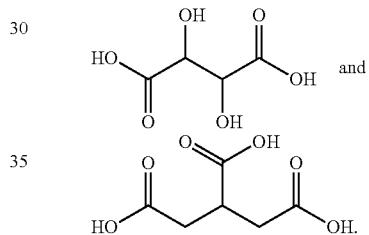

Since the monomers of formula I, II, II and/or IV may have chiral centers, it will be understood by a person skilled in the art that the monomers will possibly consist of a practically pure enantiomer or of a mixture of stereoisomers.

In another embodiment of the disclosure, $R^5$ is $C_3$-$C_{10}$cycloalkylene, $C_1$-$C_{10}$alkylene, $C_2$-$C_{10}$alkenylene, $C_2$-$C_{10}$alkynylene, said latter 3 groups being straight-chained or branched and/or interrupted by one, two or three $C_3$-$C_6$ cyclic moieties therein, wherein one or more of the carbon atoms may be replaced by oxygen, and said 4 groups being optionally substituted by one to six groups selected from OH, halo, $OR^4$ or $R^4$, in which $R^4$ is selected from $C_1$-$C_6$alkyl, $C_2$-$C_6$alkenyl, $C_2$-$C_6$alkynyl or $C_3$-$C_6$cycloalkyl. In further embodiment, the monomer of formula V is selected from

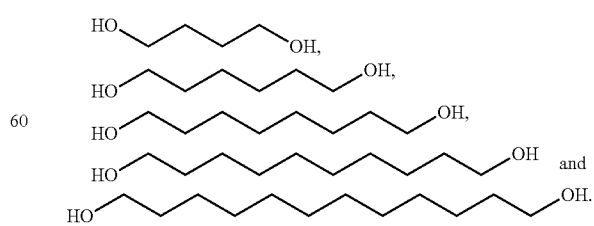

Since the monomers of formula V may have chiral centers, it will be understood by a person skilled in the art that the monomers will possibly consist of a practically pure enantiomer or of a mixture of stereoisomers.

In another embodiment of the present disclosure, the monomer of formula V is polyethylene glycol, polypropylene glycol or a poly-ε-caprolactone. In a further embodiment, the monomer of formula V is polyethylene glycol. In another embodiment, the polyethylene glycol or poly-ε-caprolactone is PEG 200, PEG 400, PEG 600, PEG 1000, PEG 2000, PEG 6000 or poly-ε-caprolactone diol of molecular weight range 500-2000D.

In another embodiment of the disclosure, n is an integer from 7 to 18. In a further embodiment, n is an integer from 7 to 10. In another embodiment, n is 7.

In another embodiment of the present disclosure, m is an integer from 1 to 10. In a further embodiment, m is an integer from 1 to 5. In another embodiment, m is 1.

In an embodiment of the present disclosure, $R^6$ and $R^7$ are $C_1$-$C_6$alkyl. In a further embodiment, $R^6$ and $R^7$ are $CH_3$.

In an embodiment of the present disclosure, the crosslinker of the formula VI is

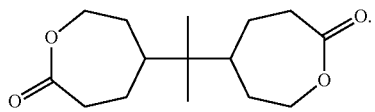 [SMILES: CC(C)(C1CCOC(=O)CC1)C1CCOC(=O)CC1]

In an embodiment of the present disclosure, the photosensitive compound is selected from

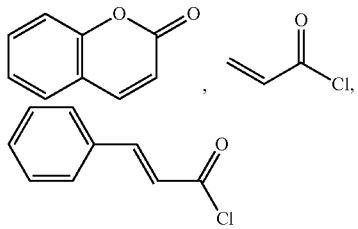

and derivatives thereof. It will be understood by a person skilled in the art that a photosensitive compound is a compound which will begin a polymerization reaction upon exposure to a photochemical stimulus. The mechanism of polymerization may proceed by radical chain reaction, cationic polymerization or anionic polymerization. Therefore, included in the disclosure, is any photosensitive compound that polymerizes upon exposure to a photochemical stimulus and are well known in the art.

In another embodiment of the present disclosure, the polymer is crosslinked with UV, laser or visible light.

The present disclosure also includes a biodegradable and biocompatible elastomeric polymer comprising a condensation polymer of an organic di-, tri- or tetra-carboxylic acid and an organic diol, said condensation polymer being either
(a) thermally crosslinked with a bis- or tri-lactone; or
(b) reacted with a photosensitive compound to form a photosensitive condensation polymer which is photocrosslinked, to provide the biodegradable and biocompatible elastomeric polymer.

The organic di-, tri- or tetra-carboxylic acid and organic diol may be any such compound that is desirably natural in origin and degrades to non-toxic by-products. Suitably the by-products are also water soluble.

In a suitable embodiment of the present disclosure, the organic di-, tri- or tetra-carboxylic acid comprises saturated or unsaturated alkyl, alkylene, cycloalkyl or cycloalkylene groups. The organic di- or tri-carboxylic acid may also comprise one or more, suitably one to two, hydroxyl groups.

In an embodiment of the disclosure, the alkyl or cycloalkyl groups of the organic di-, tri- or tetra-carboxylic acid contain between 2 and 10 carbons atoms. In another embodiment of the disclosure, the organic di-, tri- or tetra-carboxylic acid is mesaconic acid, tartaric acid, aconitic acid, tricarballylic acid, malic acid, trans-aconitic acid, citric acid, agaric acid, citraconic acid, fumaric acid, pimelic acid, suberic acid, azelaic acid, sebacic acid, glutaric acid, oxalic acid, 1,1,12,12-dodecanetetracarboxylic acid, 1,2,3,4-butanetetracarboxylic acid, cyclobutane-1,2,3,4-tetracarboxylic acid, meso-butane-1,2,3,4-tetracarboxylic acid, 1,1,2,3-propanetetracarboxylic acid or 1,1,3,3-propanetetracarboxylic acid. In a subsequent embodiment of the disclosure, the organic di-, tri- or tetra-carboxylic acid is tartaric acid or tricarballylic acid.

In an embodiment of the disclosure, the organic diol contains between 2 and 30 carbon atoms. In a further embodiment of the disclosure, the organic diol comprises saturated or unsaturated alkyl or cycloalkyl groups. In another embodiment of the disclosure, the diol comprises a linear, aliphatic and saturated diol with terminal hydroxyl groups. In a suitable embodiment of the disclosure, the organic diol is 1,4-butanediol, 1,6-hexanediol, 1,8-octanediol, 1,10-decanediol or 1,12-dodecanediol. In a suitable embodiment of the disclosure, the organic diol is 1,6-hexanediol, 1,8-octanediol, 1,10-decanediol or 1,12-dodecanediol.

In another embodiment of the disclosure, the organic diol is a polyethylene glycol or polypropylene glycol. In a suitable embodiment of the disclosure, the diol is a polyethylene glycol and can be PEG 200, PEG 400, PEG 600, PEG 1000, PEG 2000 or PEG 6000. In a further embodiment, the organic diol is poly-ε-caprolactone diol (of molecular weight range 500-2000D).

In an embodiment of the disclosure, the bis- or tri-lactone comprises two or three lactone rings. In a subsequent embodiment of the disclosure, the lactone rings are between 7 and 18 member rings. In another embodiment of the disclosure, the lactone rings are fused together. In a subsequent embodiment of the disclosure, the lactone rings are connected by a carbon linker. In an embodiment of the disclosure, the bis- or tri-lactone is bis-ε-caprolactone. Other lactones are well known in the art,[12] and these are included within the scope of the present disclosure.

In an embodiment of the disclosure, the condensation polymer is prepared by the reaction between an organic di- or tri-carboxylic acid and an organic diol. In an embodiment of the disclosure, the organic di- or tri-carboxylic acid and organic diol are present in a ratio (acid:diol) of between about 70:30 to about 30:70 (mol/mol). In a suitable embodiment of the disclosure, the organic di- or tri-carboxylic acid and the organic diol are present in a ratio (acid:diol) of about 50:50 (mol:mol). In another embodiment of the disclosure, stannous octoate is present in the reaction to form the condensation polymer. In a subsequent embodiment of the disclosure, stannous octoate is present in the range of between about $1.4 \times 10^{-5}$ mol to about $1.4 \times 10^{-3}$ mol, for every mole of condensation polymer formed. In a subsequent embodiment of the disclosure, stannous octoate is present at about $1.4 \times 10^{-4}$ mol, for every mole of condensation polymer formed. In another embodiment of the disclosure, the organic di- or tri-carboxylic acid and the organic diol are reacted at a temperature of between about 80 to about 160° C. to form the condensation polymer. In another embodiment of the disclosure, the organic di- or tri-carboxylic acid and the organic diol are reacted at a temperature of about 140° C. to form the condensation polymer.

In another embodiment of the disclosure, the thermal crosslinking can be performed at a temperature of between about 80 to about 140° C. for a period of between about 8 to about 24 hours. In an embodiment of the present disclosure, the elastomeric polymer is formed from the thermal crosslinking of the condensation polymer and the bis- or tri-lactone are present in a ratio of between about (condensation polymer:lactone) 20:1 to about 1:1 (w/w). In a suitable embodiment of the disclosure, the condensation polymer and the bis- or tri-lactone present in a ratio of between about (condensation polymer:lactone) 16:1 to about 4:1 (w/w). In an embodiment of the disclosure, the mechanical properties of the elastomeric polymer is controlled by changing the condensation polymer:lactone ratio.

In another embodiment, the present disclosure includes a biodegradable and biocompatible elastomeric polymer comprising a condensation polymer of an organic di- or tri-carboxylic acid and an organic diol, wherein said condensation polymer is reacted with a photosensitive compound to form a photosensitive condensation polymer which is photocrosslinked.

In an embodiment of the disclosure, the photosensitive compound is coumarin or a coumarin-derivative, a cinnamate or a cinnamate derivative or an acrylate or an acrylate derivative. In a suitable embodiment of the disclosure, the photosensitive compound is an acrylate group or an acrylate derivative. In a subsequent embodiment, the photosensitive compound is acroyl chloride. Different photopolymerizable end groups have previously been used to incorporate into the chain ends of polymers for the purpose of UV photocrosslinking,[30,31] and these groups are included within the scope of the present disclosure. In an embodiment of the disclosure, the condensation polymer and the photosensitive compound are present in a ratio of between about (condensation polymer:photosensitive compound) 1:10 to about 1:1 (mol/mol). In a subsequent embodiment of the disclosure, the condensation polymer and the photosensitive compound are present in a ratio of between about (condensation polymer:photosensitive compound) 1:3 to about 1:1 (mol/mol). In a subsequent embodiment of the disclosure, a photoinitiator is used to initiate the photocrosslinking process upon being irradiated. In another embodiment of the disclosure, the photoinitiator is 2,2-dimethoxy-2-phenyl-acetophenone or other acetophenone derivatives, camphorquinone or camphorquinone derivatives or Eosin dye. These and other photoinitiators are well known in the art,[32] and these photoinitiators are included within the scope of the present disclosure.

In a subsequent embodiment of the disclosure, the photosensitive compound is acroyl chloride and the condensation polymer is reacted with acroyl chloride to form the photosensitive condensation polymer which is an acrylated condensation polymer.

In an embodiment of the disclosure, the photosensitive condensation polymer is photocrosslinked upon exposure to UV or laser light. In a subsequent embodiment of the disclosure, the UV or laser light has a wavelength suitable for causing photocrosslinking, typically between about 200 to about 700 nm. In a suitable embodiment of the disclosure, the photosensitive condensation polymer is photocrosslinked upon exposure to UV light.

In another embodiment of the disclosure, the photosensitive condensation polymer is photocrosslinked upon exposure to visible light. In an embodiment of the disclosure, the visible light has a wavelength of about 380 nm to about 750 nm, optionally about 400 nm to about 700 nm.

In another embodiment of the disclosure, the visible light source used to photocrosslink the photosensitive condensation polymer is any source that produces visible light within about 380 nm to about 750 nm, optionally about 400 nm to about 700 nm, such as incandescent light bulbs, xenon lamps, laser light sources, mercury lamps and sunlight. In another embodiment, the incandescent light is produced from a light bulb, such as a tungsten light bulb.

In an embodiment of the disclosure, visible light efficiently photocrosslinks the photosensitive condensation polymers of the disclosure. It will be apparent to those skilled in the art that many transparent polymeric materials do not absorb visible light and therefore, visible light is able to penetrate to regions deep within polymeric material and photocrosslink those regions. Therefore, visible light is able to photocrosslink a much larger area and volume of polymer at a faster rate.

In an embodiment of the disclosure, the photocrosslinking of the photosensitive condensation polymer is performed at a temperature of between about 20 to about 40° C. In a suitable embodiment of the disclosure, the photocrosslinking is performed at about room temperature.

In an embodiment of the disclosure, the photocrosslinking is performed at a light source distance from between about 1 to about 20 cm. In a suitable embodiment of the disclosure, the photocrosslinking is performed at a light source distance of about 10 cm.

In an embodiment of the disclosure, when UV light or laser light is used for photocrosslinking, the photosensitive condensation polymer is exposed to the light for a period of between about 1 to about 20 minutes. In a suitable embodiment of the disclosure, the photosensitive condensation polymer is exposed to the UV light or laser light for about 5 to about 15 minutes, optionally about 5 to about 10 minutes or about 5 minutes.

In an embodiment of the disclosure, when visible light is used for photocrosslinking, the photosensitive condensation polymer is exposed to the light for a period of between about 1 to 20 minutes. In a suitable embodiment of the disclosure, the photosensitive condensation polymer is exposed to the visible light for about 5 to about 15 minutes, optionally about 5 to about 10 minutes or about 5 minutes.

In a further embodiment of the disclosure, the visible light source used to photocrosslink the photosensitive condensation polymer is any source that produces visible light within about 380 nm to about 750 nm, such as incandescent light bulbs, xenon lamps, laser light sources, mercury lamps and sunlight. In a further embodiment, the incandescent light bulb is a tungsten light bulb having a wattage of about 10 watts to about 200 watts. In a further embodiment, the tungsten light bulb has a wattage of about 50 watts to about 15 watts. In another embodiment, the tungsten light bulb has a wattage of about 100 watts.

In an embodiment of the disclosure, the photocrosslinking is conducted at temperatures and pH values near physiological ranges when loaded with thermo-sensitive pharmaceuticals like proteins and other heat-sensitive pharmaceuticals. In a subsequent embodiment of the disclosure, the photocrosslinking proceeds very rapidly and does not require a long curing time for complete crosslinking. In another embodiment of the disclosure, the degree of crosslinking, and the mechanical properties of the photocrosslinked elastomeric polymer is manipulated by changing the density of the photosensitive termini in the condensation polymer.

In another embodiment of the disclosure, the elastomeric polymer is amorphous with homogenous degradation and is able to provide controlled release of incorporated substances. In a suitable embodiment of the disclosure, the biodegradable and biocompatible elastomeric polymer has a glass transition temperature ($T_g$) below body temperature and room temperature. In a subsequent embodiment of the disclosure, the biodegradable and biocompatible elastomeric polymer has a glass transition temperature ($T_g$) below 0° C. In a suitable embodiment of the disclosure, the biodegradable and biocompatible elastomeric polymer has a glass transition temperature ($T_g$) from between 0° C. to −15° C.

In another embodiment of the disclosure, the biodegradable and biocompatible elastomeric polymers of the present disclosure are useful for coating metallic biomedical devices. In a suitable embodiment of the present disclosure, the biodegradable and biocompatible elastomeric polymers of the present disclosure are useful for coating needles, stents, catheters and tissue scaffolds, in particular for tissue engineering and regenerative nerve endings. It is well known in the art that elastomeric polymers are useful in the regeneration of nerve endings. One example of such is found in U.S. Application Pub. No. 2006/0287659. Thus, the disclosure includes a method of regenerating nerve endings wherein a nerve ending is regrown in a conduit comprised of the biodegradable and biocompatible elastomeric polymers of the present disclosure. In an embodiment of the disclosure, the biodegradable and biocompatible elastomeric polymers are useful as implants and scaffolds for soft tissues because they are degradable, porous, highly permeable, able to maintain a desired shape and modulate biological responses. In a subsequent embodiment of the disclosure, the biodegradable and biocompatible elastomeric polymers possess the required elasticity for use in tissue scaffolds to enable them to respond to the mechanical stimuli and adapt to the dynamic environment where it is implanted.

In another embodiment of the disclosure, a pharmaceutical agent is incorporated into the photosensitive condensation polymer prior to exposure to UV or laser light photocrosslinking. Accordingly, the incorporation of the pharmaceutical agent is accomplished without need for a solvent which avoids the use of irritating solvents and also offers more stability for loaded pharmaceuticals and proteins.

In a subsequent embodiment, the biodegradable and biocompatible elastomeric polymers of the present disclosure are useful as artificial biomaterials. In a suitable embodiment, the biodegradable and biocompatible elastomeric polymers are useful as a skin substitute or burn dressing. It is well known in the art that elastomeric polymers are useful as a skin substitute,[34] and this reference is herein incorporated. Thus, the disclosure includes a method of using the biodegradable and biocompatible elastomeric polymers as skin substitutes or burn dressings comprising the formation of a thin film of the polymer for use as the dressing. In another embodiment of the present disclosure, the biodegradable and biocompatible elastomeric polymers are useful in the manufacture of implantable drug delivery devices. In an embodiment of the disclosure, the photocrosslinked biodegradable and biocompatible elastomeric polymers are useful for drug delivery of all conventional and synthetic pharmaceutical agents. In a subsequent embodiment of the disclosure, the photocrosslinked biodegradable and biocompatible elastomeric polymers are useful for the delivery of both hydrophilic and hydrophobic pharmaceutical agents, and in particular anti-cancer pharmaceuticals. In another embodiment of the present disclosure, the photocrosslinked biodegradable and biocompatible elastomeric polymers are useful for the delivery of heat sensitive pharmaceutical agents. In a suitable embodiment of the disclosure, the photocrosslinked biodegradable and biocompatible elastomeric polymers are useful for the delivery of cytokines, hormones, angiogenesis inhibitors, angiogenic factors, growth factors and other immuno-modulators. In a subsequent embodiment of the disclosure, the pharmaceutical agents are loaded into the photocrosslinked elastomers alone or mixed/lyophilized with other protein stabilizing agents like non-crystallizing sugars (sucrose and trehalose), mannitol, albumins, surfactants, or any other pharmaceutical excipients. Thus, the present disclosure includes a method for treating a disease treatable with a pharmaceutical agent by administering to a person a biodegradable and biocompatible elastomeric polymer containing such pharmaceutical agent.

It will be apparent to those skilled in the art that visible light is generally not destructive to the drugs which may be embedded within the elastomeric polymer. The visible light polymerization conditions are also sufficiently mild to be carried out in the presence of other biological materials, for example, for encapsulating cells and proteins in drug screening, or in biosensing applications. Furthermore, visible light is able to penetrate deep within tissues because visible light scatters less and is absorbed less by the tissue. Consequently, visible light photocrosslinking may limit the need for invasive surgical procedures by allowing trans-tissue polymerizations, whereby a photosensitive condensation polymer of the present disclosure is injected subcutaneously or even subdermally and irradiated through the skin to polymerize the elastomeric polymer in situ.

In another embodiment of the present disclosure, methods of preparing a thermally crosslinked and photocrosslinked biodegradable and biocompatible elastomeric polymer are disclosed.

In an embodiment of the disclosure, tartaric acid and transaconitic acid are naturally occurring organic carboxylic acids which both degrade to water-soluble by-products with no toxicity.

In a suitable embodiment of the disclosure, the elastomeric polymer can have only hydrophilic character. In a subsequent embodiment of the disclosure, the elastomeric polymer can have both hydrophilic and lipophilic character. Accordingly, the hydrophilic character of the polymer makes the elastomeric polymer more cell friendly due to the low contact angle with water and less susceptibility to protein adsorption. The free hydroxyl groups on the surface of the elastomeric polymer chains helps in rebelling protein.

In another embodiment of the disclosure, the mechanical properties and the degree of crosslinking of the elastomeric polymer can be easily manipulated by controlling the amount of the bis- or tri-lactone, the chain length of the organic diols, time of crosslinking and crosslinking temperature used. Accordingly, in an embodiment of the disclosure, the mechanical elastic properties of the elastomeric polymer and its high surface contact angle with water are all properties which enable transfer of cells stimuli without irritation and prevent or decrease fiber tissue formation resulting from surface protein adsorption.

Accordingly, in an embodiment of the present disclosure, a method of preparing a biodegradable and biocompatible elastomeric polymer comprises combining an organic di- or tri-carboxylic acid and an organic diol to form a condensation polymer, and combining the condensation polymer with a bis- or tri-lactone, so that a thermally crosslinked biodegradable and biocompatible elastomeric polymer is formed. In another embodiment of the disclosure, the method comprises thermally crosslinking the condensation polymer with a bis- or tri-lactone at a temperature of between about 80 to about 140° C. for a period of between about 8 to about 24 hours.

In an embodiment of the disclosure, the method comprises photocrosslinking a photosensitive condensation polymer with exposure to UV or laser light at room temperature in the presence of a photoinitiator. In a subsequent embodiment, the method comprises photocrosslinking a photosensitive condensation polymer with exposure to UV for a period of between about 1 to about 20 minutes and at a light source distance between about 1 to about 20 cm.

In another embodiment of the disclosure, the method comprises photocrosslinking a photosensitive condensation polymer upon exposure to visible light at room temperature in the presence of a photoinitiator. In a subsequent embodiment, the method comprises photocrosslinking a photosensitive condensation polymer with exposure to visible light for a period of between about 1 to about 20 minutes and at a light source distance between about 1 to about 20 cm.

The following non-limiting examples are illustrative of the present disclosure:

EXAMPLES

Reagents and Materials

L-tartaric acid, D-tartaric acid, transaconitic acid, tricarballylic acid, 1,4-butandiol, 1,6-hexanediol, 1,8-octanediol, 1,10-decanediol and 1,12-dodecanediol were obtained from Sigma-Aldrich. Other chemicals used in the synthesis and purification of elastomers were tin 2-ethylhexanoate (SnOct) stannous octoate, acetone and methanol from Sigma-Aldrich. The chemicals used in the preparation of the cross-linker 2,2-bis(ε-caprolactone-4-yl)-propane (BCP) include 2,2-bis(4-hydroxycyclohexyl)propane from TCI America, chromium trioxide, m-chloroperoxybenzoic acid (mCPBA), acetone, and 2-heptanone were obtained from Sigma-Aldrich. Other chemicals used include 2-propanol, dichloromethane, and glacial acetic acid from Fisher.

Proton Nuclear Magnetic Resonance ($^1$H-NMR) of the condensation polymer was run in chloroform-$d_6$ or acetone-$d_6$ to determine both composition and number average molecular weight using a Bruker Avance-500 MHz Spectrometer. Tertramethylsilane was used as the internal reference.

The FT-IR experiments were acquired on a Bruker FT-IR spectrometer (model Tensor 27) using NaCl cells. IR spectra and data were analyzed using Opus software.

Molecular Weight Analysis and Molecular masses were determined by gel permeation chromatography using Agilent 1100 system connected to PD 2000 DLS light scattering detector and equipped with Phenogel linear (2) 5μ GPC column. Tetrahydrofuran was used as an eluent. Samples were dissolved in THF (10 mg/ml), the injected volume was 25 μl and the flow rate was 1 ml/min. Mono-dispersed polystyrene (Aldrich) standards were used for primary calibration.

Thermal analysis experiments were carried out using DSC-Seiko 210 equipped with nitrogen cooling system. The samples were run at a heating rate of 10° C./min using cycle heating from ambient to −50° C. to 150° C. to −50° C. to 150° C., with the glass transition temperature ($T_g$) measured from the second heating cycle. The DSC instrument was calibrated using indium and gallium standards. The enthalpies, glass transitions temperatures, and melting endotherms were all determined using the Seiko DSC analysis program.

Sol content (Q) calculations of the elastomers and the degree of swelling (R) were measured in triplicate as follows. Disc-shaped sample (3 mm in thickness and 10 mm in diameter) with weight $W_1$, diameter $D_1$ and thickness $T_1$ was dipped in 20 ml of DCM for 24 h. The sample was then removed and the weight of the disk $W_2$, its diameter $D_2$ and thickness $T_2$ were recorded before drying the disc. The disc was then dried in a vacuum oven at 40° C. under 4000 Pa for 7 days until a constant weight was achieved. The weight $W_3$, the diameter $D_3$, and the thickness $T_3$ were all recorded. The sol content was calculated as follows: $(Q)=[(W_1-W_3)/W_1]\times 100\%$. The swelling degree (R) for the corresponding gel was calculates as $(R)=[(W_2-W_3)/W_3]\times 100\%$. The mean and standard deviations from triplicates samples were calculated.

End group analysis was conducted to determine the hydroxyl number of the prepared condensation polymers by catalyzed acetylation.[37] In a 125 ml conical flask, 1 gram of the prepared condensation polymer was dissolved in 1 ml acetone. Five milliliters of 2% (w/v) 4-dimethylaminopyridine in pyridine followed by 2 ml of 25% (v/v) acetic anhydride in pyridine, were transferred to the solution and mixed well. After 20 minutes, 25 ml of distilled water was added to the mixture followed by the addition of three drops of 1% phenolphthalein solution. The solution was then titrated against 0.5 N Sodium Hydroxide until the end point is reached indicated by pink color formation. A blank control experiment was also carried out following the exact procedure but without the addition of the condensation polymers. The number of millimoles of hydroxyl group present in the condensation polymer samples is given by N ($V_b-V_s$), where $V_b$ and $V_s$ are the milliliters of sodium hydroxide solution of N normality required to titrate the blank and the condensation polymer sample, respectively. The results of end group analysis were compared with that obtained from weight average molecular weight analysis using GPC.

Tensile mechanical tests were conducted using Instron model In-Spec 2200 tensile tester equipped with Merlin Data Management Software. The machine was equipped with 500 N load cell. The mechanical properties of the elastomers were carried out on slabs (100×6×3 mm) and the crosshead speed was set at 50 mm/min while the sampling rate was set at 0.833 mm/sec. All specimens were tested at room temperature. Values of the stress and the strain were recorded and Young's Modulus values were calculated from the initial slope of the stress-strain curve. Three triplicate of each sample were measured for which the mean and the standard deviation were calculated.

Example 1

Preparation of 1:1
poly(1,8-octanediol-L-tartaric)ester (POT)
Condensation Polymer Solvent free polymerization was carried out in a three neck round bottom flask equipped with a condenser, gas inlet and a magnetic stirrer. Into the flask, and under argon atmosphere, a 1:1 molar ratios of L-tartaric acid (0.105 M) and 1,8-octanediol (0.105 M) and an amount of SnOct equivalent to $1.4\times10^{-4}$ mol for each 1 mol of the monomer were transferred, mixed and heated at 140° C. using silicone oil bath for 1 hour. The reaction was then run under vacuum for 2 more hours. The resulting molten mass of the prepared crude condensation polymer was then dissolved in chloroform, filtered, precipitated in cold anhydrous ethyl ether, and dried under vacuum overnight. The final product was characterised using Nuclear Magnetic Resonance (NMR), Mass Spectroscopy (MS), Fourier Transform Infra Red Spectroscopy (FT-IR), Gel Permeation Chromatography (GPC) and Differential Scanning calorimetry (DSC).

Figure 2:
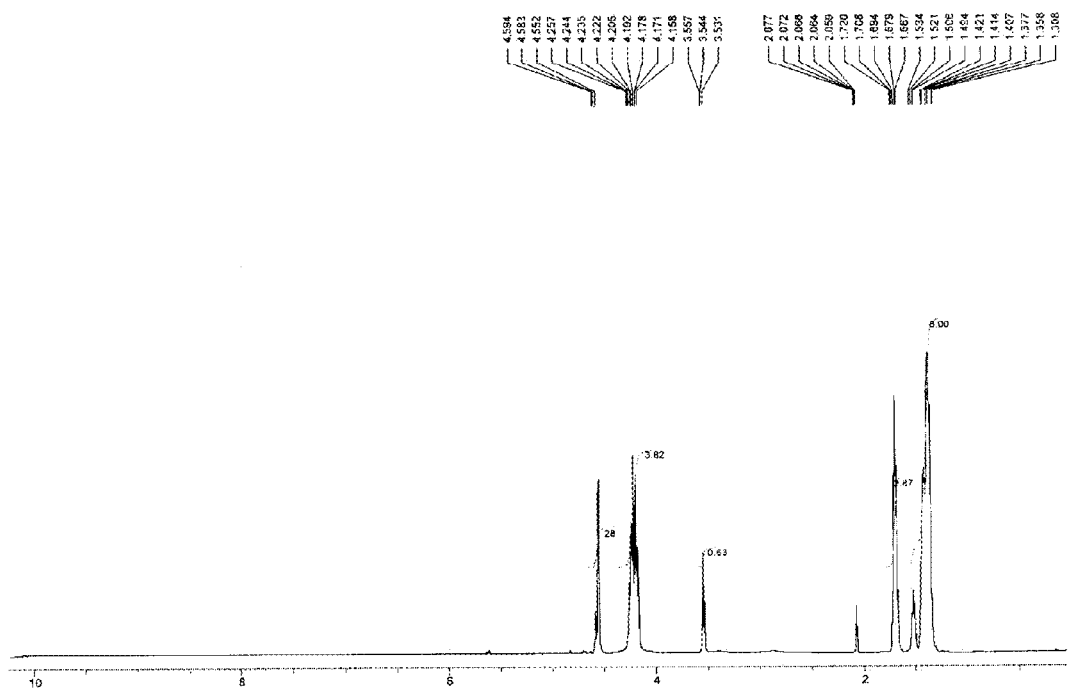
FIG. 2 is a $^1$H-NMR spectrum of a condensation polymer of tartaric acid and 1,8-octanediol (POT)

The GPC molecular weight analysis of the prepared condensation polymer resulted in Mw=2675 g/mol, Mn=1278 g/mol and a polydispersity value of Mw/Mn=2.1. The molecular weights measured via GPC values matched the theoretical condensation polymer molecular weight calculations estimated using $^1$H-NMR. The average molecular weight calculated was 1247 g/mol and estimated based on the degree of the polymerization of both monomers. FIG. 2 shows the $^1$H-NMR of POT condensation polymer which also confirmed its composition as being 53 mol % 1,8-octanediol and 47 mol % of L-tartaric acid measured using the ratio of the integrals at the chemical shift of 1.3 ppm which corresponds to 1,8-octanediol methylene protons resonances to that at 4.5 ppm which corresponds to L-tartaric methane protons resonances.

The $^1$H NMR spectrum of POT shows peaks at 1.3, 1.5, and 1.7 ppm; these three peaks are assigned to the methylene protons. The peaks at 3.5 ppm are attributed to the hydroxylprotons at the end of the diol monomer. The protons on the methine group (CH) adjacent to the ester bond were attributed to the peak at 4.2 ppm, and the peak at 4.5 ppm was assigned to the α-hydrogens on the L-tartaric acid.

Figure 3:
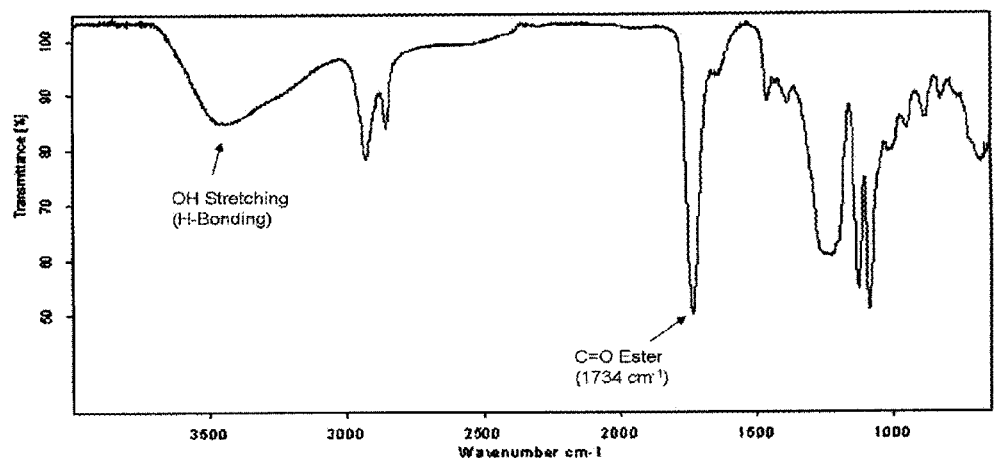
FIG. 3 is a FT-IR spectrum of a condensation polymer of tartaric acid and 1,8-octanediol (POT)

The FT-IR analysis of POT is shown in FIG. 3 which confirms the formation of ester bonds. The peaks within 1690-1750 cm$^{-1}$ were attributed to carbonyl (C=O) groups. A relatively sharp peak centered at 1735 cm$^{-1}$ was found in the spectrum which was attributed to the (C=O) ester group. The absorption bands at 2928 cm$^{-1}$ and 2856 cm$^{-1}$ were attributed to C—H stretching vibrations. The broad peak at 3600-3100 cm$^{-1}$ was attributed to the OH stretching vibrations and its broadening is an indication that the hydroxyl groups are involved in hydrogen bonded. The non-covalent inter- and intra-molecular interaction of hydrogen bonding and Van der Waals attractive forces were expected to affect the thermal and mechanical properties of the polyester. Finally, the peaks from 1300-1000 cm$^{-1}$ were attributed to C—O stretching vibrations.

The DSC thermal analysis of the prepared POT condensation polymer showed that a semicrystalline condensation polymer was produced with a corresponding Tg of −16.0° C. and a melting endotherm of 57.2° C., with latent heat of fusion of 36.39 J/g.

In a like manner, the preparation of condensation polymers from diols and di- and tricarboxylic acids having different chain lengths, for example ranging from 4 carbons to 12 carbons. Accordingly different di- and tri-carboxylic acids (transaconitic, tricarballylic, . . . ) were reacted with different diols (1,4-butandiol, 1,6-hexanediol, 1,8-octanediol, 1,10-decanediol and 1,12-dodecanediol, PEG 400, PEG 6000 . . . etc) to provide the corresponding condensation polymers.

Example 2

Synthesis of the Elastomeric Polymer (a) Procedure:

The following procedure describes the steps involved in preparing the elastomer using a 4:1 weight ratio of POT: BCP respectively, as seen in FIG. 1. In a dry silanized glass ampoule, 1 g of BCP was left in the preheated oven for 5-10 minutes to melt at 160° C. A molten mass of 4 g polyester condensation polymer (POT) and an amount of SnOct equivalent to 1.4×10$^{-4}$ mol for each 1 mol of the monomer were added to the ampoule. The content was mixed using a vortex mixer and the ampoule was sealed under vacuum. The ampoule was then left in the vacuum oven at 120° C. for 1 hour and then the seal was broken and the highly viscous liquid was poured into rectangular Teflon moulds (100×6×3 mm), covered, left in the vacuum oven at 120±5° C. under 10 mmHg vacuum for 18 hours. The elastomeric slabs were then removed from the mould and characterized using DSC, FT-IR and in vitro degradation and tensile testing before and during the degradation study. Table 1 reports the different ratios of both polyester condensation polymer POT and BCP used to prepare the elastomers.

The purified POT was crosslinked in different weight ratios with the BCP monomer (FIG. 1). Table 1 reports the different weight ratios of POT and BCP used to prepare 4 different elastomers with different mechanical properties. A summary of the corresponding Tg is shown in Table 2. The data shows that the higher amount of BCP used in crosslinking POT, the higher the Tg of the elastomer ranging from −9.3 to −4.8° C. The thermal analysis also demonstrated that amorphous Elastomers were prepared with no melting temperatures observed in the corresponding thermographs above room temperature The increase in Tg is usually attributed to the movement of the polymer chain segment. In general, any structure feature that restricts the chains mobility within the elastomer network will result in an increase the Tg. Thus, crosslinking becomes more efficient as more BCP was used.

In order to confirm the formation of the crosslinked networks, swelling experiments in dichloromethane were carried out. The results indicated that a true elastomer network was formed, as none of the elastomeric discs dissolved in dichloromethane. Table 3 summarizes the sol content %, (Q) and degree of swelling (R) for the prepared elastomers.

As can be seen, the gel content of the products gradually increased and the sol content decreased with increasing the BCP ratio in the elastomers. Upon increasing the BCP ratio in the reactants, more crosslinked anchors were formed and gel content increased while the corresponding sol content and degree of swelling decreased.

Degree of swelling of the corresponding gel (R) of elastomers in dichloromethane is a parameter used to characterize the crosslinking degree of the prepared elastomers. From (R) values reported in Table 3, two phenomena are worth noting. First, all of the degree of swelling ranged between 161 and 264%, which implied that the crosslinked part of the elastomeric networks i.e. the gel part, was fairly high. Second, the (R) values of the prepared elastomers increased when less amounts of the bis-lactone crosslinker, BCP, was used. More sol content in the network helped in achieving higher swelling and the results above reflected that trend.

Figure 4:
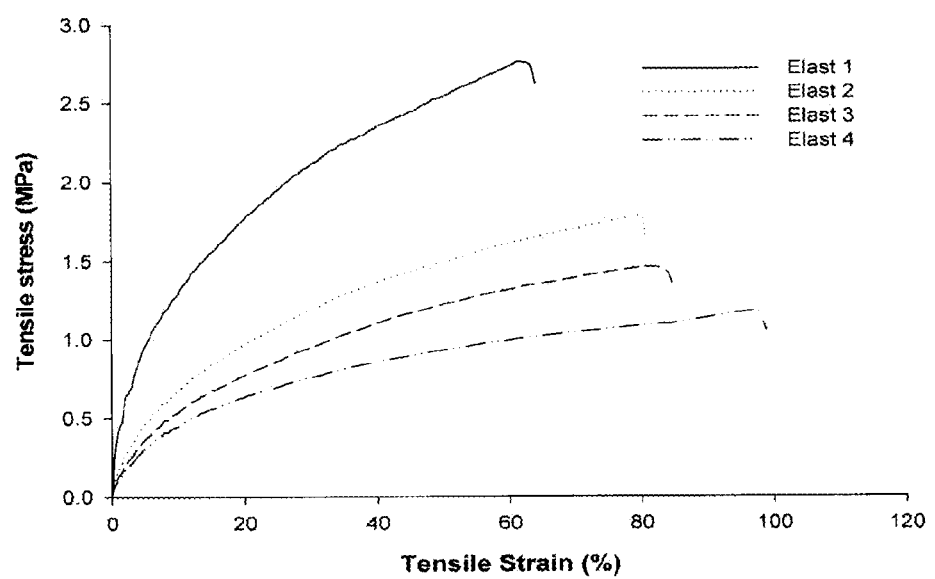
FIG. 4 is a graph showing the stress-strain behaviour of various biodegradable and biocompatible polymers using tartaric acid and 1,8-octanediol (POT), and having varying concentrations of bis-ϵ-caprolactone.

For the purpose of determining the mechanical properties of the samples reported in Table 1, slabs of those samples were subjected to tensile testing as described under experimental section. FIG. 4 shows representative stress-strain profiles for the elastomers prepared using varying BCP:POT ratios as reported in Table 1. The average values for the Young's modulus (E) extension ratio ($\lambda_b$) ultimate tensile stress (a) and ultimate tensile strain (ε) obtained from the uniaxial tensile measurements are listed in Table 4. It is clear that incorporating higher amounts of the crosslinker, BCP, resulted in tougher elastomers. This is supported by higher average E values (1.86 versus 0.52 MPa), lower average $\lambda_b$ values (1.34 versus 2.04), higher average a values (2.99 versus 1.05 MPa), and lower average $\epsilon$ values (66.62 versus 95.27%) as the BCP:POT molar ratio increased from 0.29 to 1.16. In addition, the elastomers exhibited almost Hookean behavior to failure and demonstrated mechanical properties similar to Elastic proteins which make them good candidates for soft tissue engineering purposes.[34]

The above stress-strain behaviours of tested elastomers reflected their Tg. In addition, incorporation of higher ratios of BCP resulted in a high crosslinking density and tougher Elastomers. As shown, Elast 1 is the toughest among the four prepared Elastomers indicated by its higher E value and lower $\epsilon$. On the other hand, Elast 4 with less crosslinker ratio was a soft and weak elastomeric polymer with a low E and high $\epsilon$. Based on this analysis and results, it is concluded that the mechanical properties of the elastomers can be tailored to fit different biomedical application by changing the BCP to POT ratio.

Example 3

In Vitro Degradation Studies (a) Procedures:

Slab specimens of Elast 1 and Elast 2 of the prepared elastomers reported in Table 1 were subjected to an in vitro degradation study. Each specimen was transferred into 15 ml tissue culture tube containing 12 ml of 1/15 M Phosphate Buffer Saline (PBS) at pH 7.4. The tubes were then attached to a Glas-Col's rugged culture rotator. The rotator was set at 30% rotation speed and placed in an oven at 37° C. The buffer was replaced on daily basis to ensure a constant pH of 7.4 during the whole period of the study. One set of samples representing each ratio was left without changing its buffer to monitor the change in the medium's pH with respect to time. The specimens were then dried, weighted and subjected to tensile testing at time periods of 0, 1, 2, 4, 6 and 8 weeks.

Mass loss over 0, 1, 2, 4, 6 and 8 weeks was calculated using the following formula: Mass loss=[(G1−G2)/G1]×100%, where G1 is the initial weight of the slab before degrading in the buffer (i.e. at zero time). G2 is the weight of the slab after being dried in a vacuum oven at 40° C. until constant weight obtained.

Figure 5:
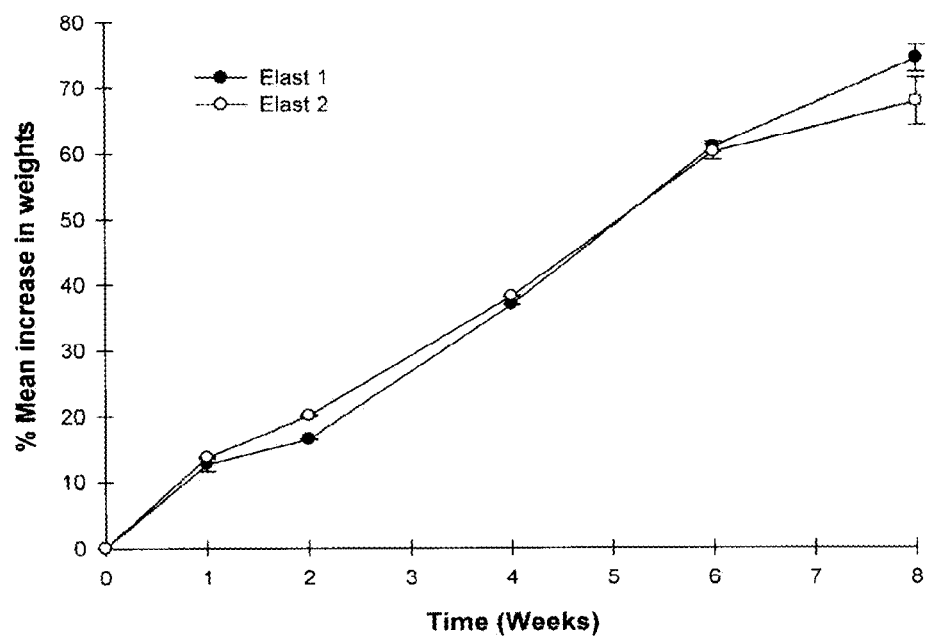
FIG. 5 is a graph showing the percentage increase in weight of two biodegradable and biocompatible polymers using tartaric acid and 1,8-octanediol (POT), and having varying concentrations of bis-ϵ-caprolactone.
Figure 6:
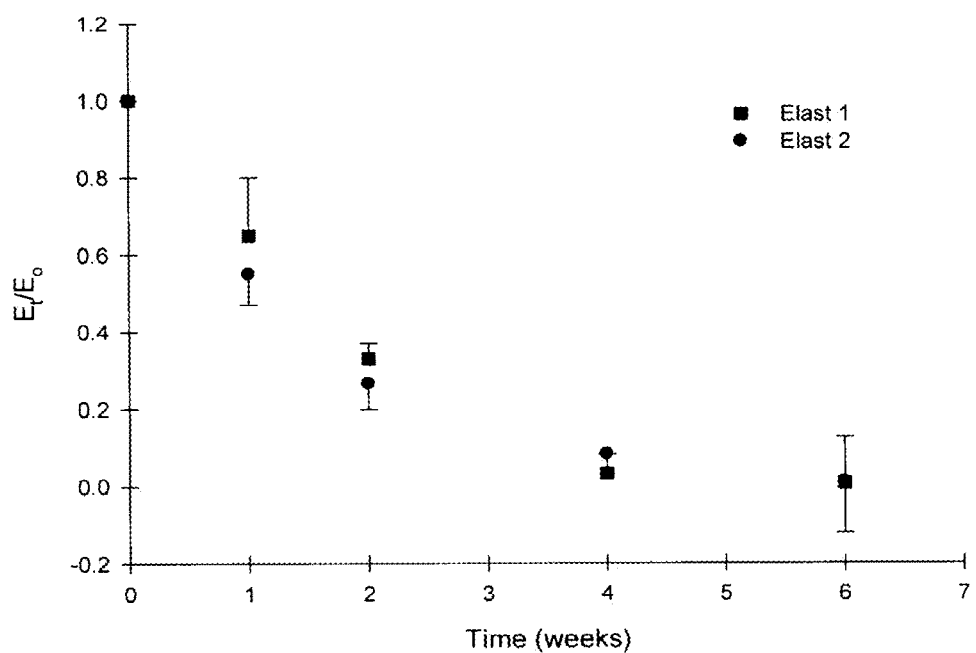
FIG. 6 is a graph showing the change in Young's Modulus with time of the polymers of FIG. 5.
Figure 7:
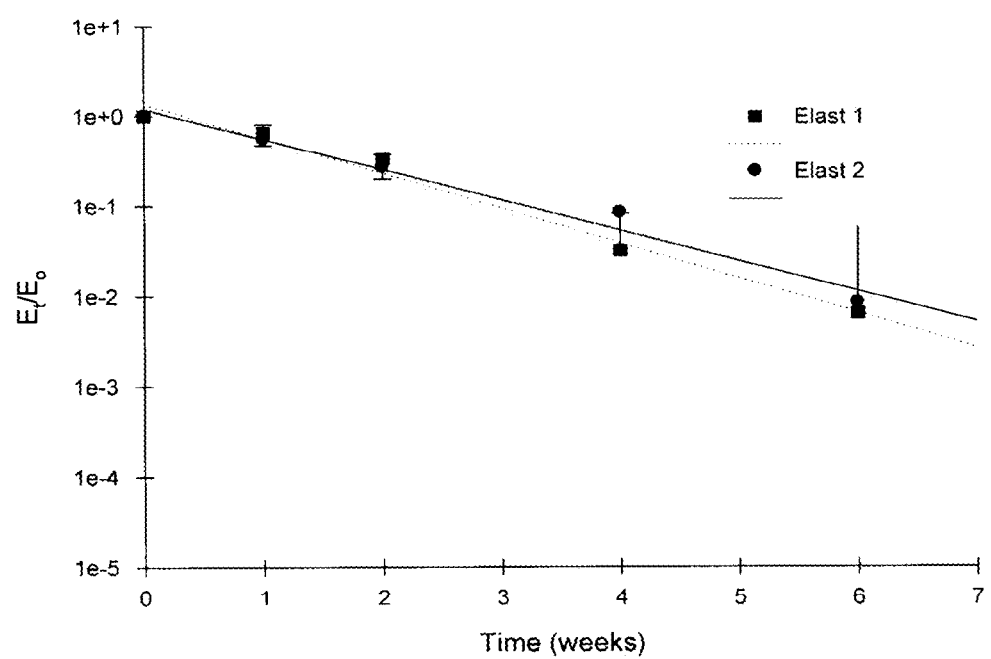
FIG. 7 is a graph showing the change in Young's Modulus with time on a log scale of the polymers of FIG. 5.
Figure 8:
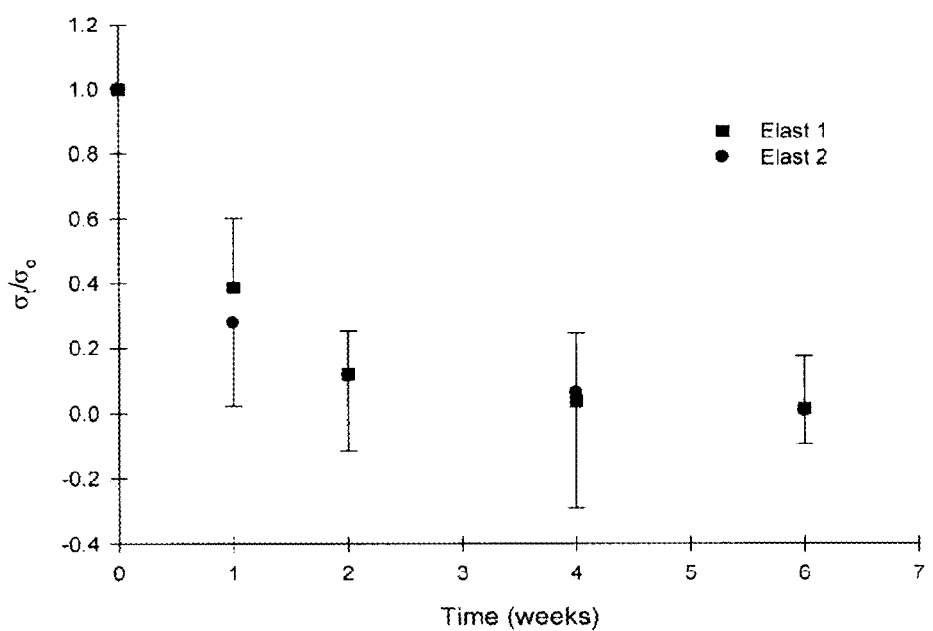
FIG. 8 is a graph showing the change in ultimate tensile stress with time of the polymers of FIG. 5.
Figure 9:
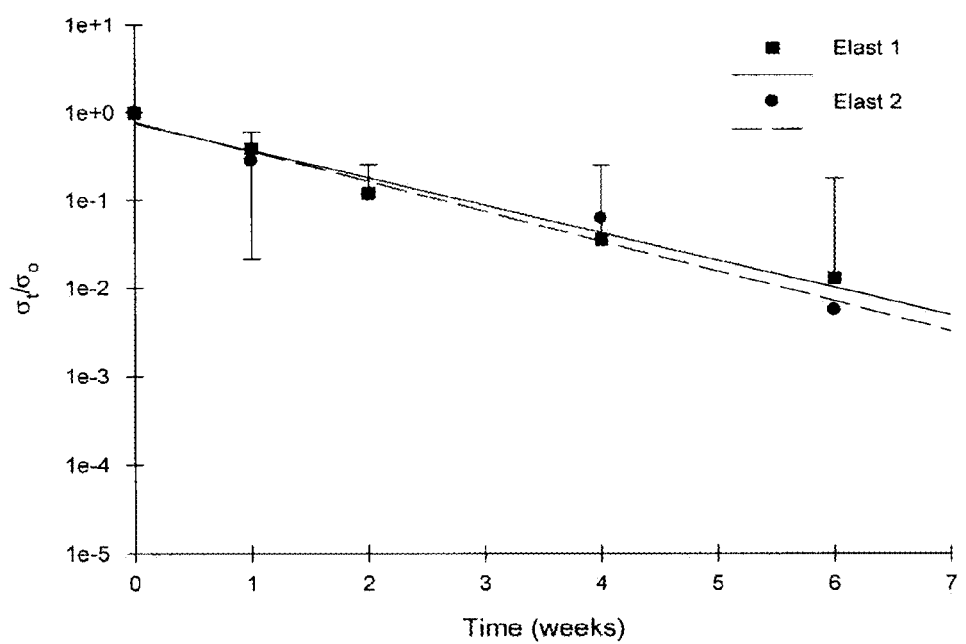
FIG. 9 is a graph showing the change in ultimate tensile stress with time on a log scale of the polymers of FIG. 5.

To investigate in-depth the changes in the mechanical properties and the degradation patterns of the prepared elastomers as a function of time, representative slab specimens of Elast 1 and Elast 2 were subjected to in vitro degradation in PBS of pH 7.4 at 37° C. FIG. 5 shows the percentage mean increase in weight of the tested slabs with respect to time over a period of 8 weeks.

The increase in the slab weight over time is attributed to water absorption from the degradation media into the slabs' bulk. When the elastomers start to degrade by non-enzymatic hydrolytic cleavage of ester bonds, accumulation of the acidic hydrolysis products will take place inside the elastomer which will accelerate the degradation rate. Furthermore, the accumulation of the hydrophilic acidic moieties act as a driving force for imbibition of water into the elastomers due to high osmotic activity, therefore the elastomers begin to swell. As shown in FIG. 5, both Elast 1 and Elast 2 increased almost 13% in weight after one week as a result of water absorption. By the end of the $8^{th}$ week, almost 60-70% weight increase was achieved as a result of water absorption.

The weight increase in the elastomers with time can be used as a measure of the rate of degradation of the products. The prepared Elastomers posses a fast degradation rate as a result of their hydrophilic nature compared to what is reported in literature. Having said that, the use of longer diol monomers and increasing BCP ratio would be a strategy to increase the degradation time depending on the biomedical application they are intended to be used for.

The mass loss data obtained after drying the slabs for Elast 1 and Elast 2 showed no remarkable loss in weight after the 8 week period (2-4%). This result is indicative of a typical bulk hydrolysis taking place which is characterized by linear decrease in molecular weight with no significant change in the mass of the polymer. Since the Elastomers are not soluble in organic solvents, it was almost impossible to monitor the decrease in molecular weight with time using GPC analysis. However, pervious studies conducted confirmed that the degradation of tartarate based polymers mainly degrades via bulk erosion mechanism.[35]

Changes in the mechanical properties of the Elastomers during the in vitro degradation period are shown in FIGS. 6 to 9. The figures show the changes in normalized values (values at time t divided by value at time 0) for both Young's modulus and the ultimate tensile stress over time. The decrease in both parameters with time followed a first-order degradation (See log scaled Figures) pattern in both Elast 1 and Elast 2 and regardless of the crosslink density or amount of BCP used. No significant change in the degradation profiles between Elast 1 and Elast 2 were observed Example 4

Preparation of acrylated
poly(1,8-octanediol-L-tartaric) ester (APOT)
Condensation Polymers (a) Procedures:

In a round bottom flask 20 g of POT (0.0166 mole) was dissolved in 200 ml of anhydrous acetone on a magnetic stirrer using a magnetic bar. The flask was sealed using a rubber septum and flushed with argon gas to remove the oxygen from the reaction environment. This was repeated every one hour throughout the experiment. The flask was then immersed in a 0° C. ice bath, after which 10 mg of 4-dimethylaminopyridine (DMAP) was added as a catalyst. A stepwise addition of 0.0166 mole of each of acryloyl chloride (ACRL) and triethylamine (TEA) was performed over a period of 12 hours at 0° C. The reaction was later continued at room temperature for another 12 hours. The reaction completion was detected using thin layer chromatography and the final solution was filtered to remove triethylamine hydrochloride salt formed during the reaction. The acrylated POT condensation polymer solution was concentrated using a rotary evaporator and further purified by precipitation in cold ethyl acetate. The purity of the final product and the disappearance of the OH group as a result of formation of the terminal C= was characterised using FT-IR, $^1$H-NMR, $^{13}$C-NMR.

The above procedure was repeated using different molar ratios of acryloyl chloride to POT in order to prepare APOT of different degrees of acrylation. So, 1:1, 2:1 and 3:1 molar ratios were used to assess the effect of the acrylation on the conversion of terminal OH in the condensation polymer into C=C.

Acrylates were chosen here because they possess greater reactivity and can undergo very rapid photopolymerization.[37] In addition, they eventually undergo degradation to acrylic acid which is extensively metabolized to water soluble components that are rapidly and safely excreted by the kidney with no possibility of bioaccumulation. The terminal hydroxyl groups in POT prepared were subjected to acrylation process using Acryloyl Chloride (ACRL) for the purpose of introducing unsaturated vinyl terminals that can be further crosslinked using UV or laser photopolymerization technology in the presence of the proper photoinitiator. The method of Hubbell was used here in which the condensation polymers were end-capped by their reaction with ACRL to introduce those C=C groups at the termini required for further UV photo-crosslinking.[32]

Figure 11:
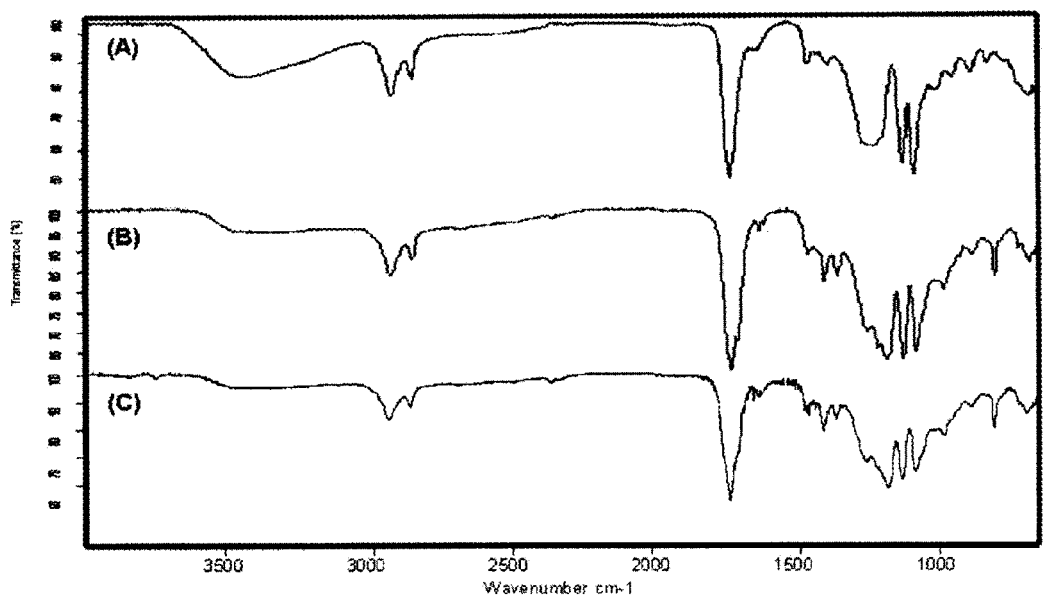
FIG. 11 is a stacked FT-IR spectrum of an acrylated condensation polymer (composed of tartaric acid and 1,8-octanediol (POT)) reacted with different molar ratios of acryloyl chloride, where (A) is non-acrylated, (B) 2:1 (acryloyl chloride to condensation polymer), (C) 3:1.

For the purpose of determining the effect of using different molar ratios of ACRL/POT in the reaction, and for the goal of determining the optimum amounts required of ACRL to undergo a complete acrylation for the terminal hydroxyl groups, different ACRL/POT molar ratios were used for that purpose. The stacked IR spectra for the acrylated condensation polymers are shown in FIG. 11. It is clear here that as the ACRL:POT molar ratio increases, the intensity of the corresponding broad OH stretching at around 3500 cm$^{-1}$ decrease. A nearly complete disappearance of the OH stretching took place upon using 3:1 molar ratios compared to minor changes with OH stretching peak in case of 2:1 molar ratios.

The previous experiments showed that the reaction of each mole of POT with 3 moles of ACRL and 3 moles of TEA resulted in a nearly complete conversion of the terminal carboxylic groups of the POT to the corresponding vinyl groups (94% based on NMR calculation).

Figure 12:
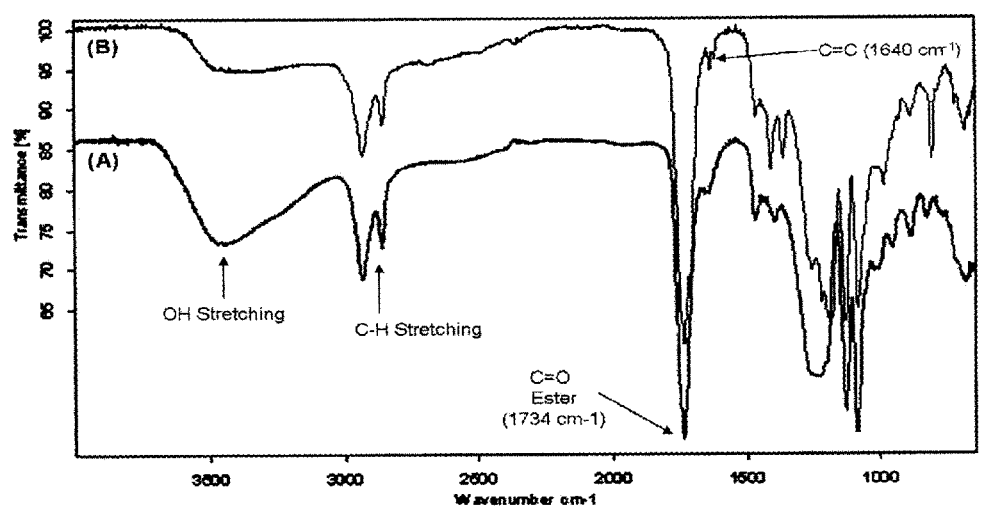
FIG. 12 is an overlapped FT-IR spectra of a condensation polymer (composed of tartaric acid and 1,8-octanediol (POT)) where (A) is before acrylation and (B) is after acrylation.
Figure 13:
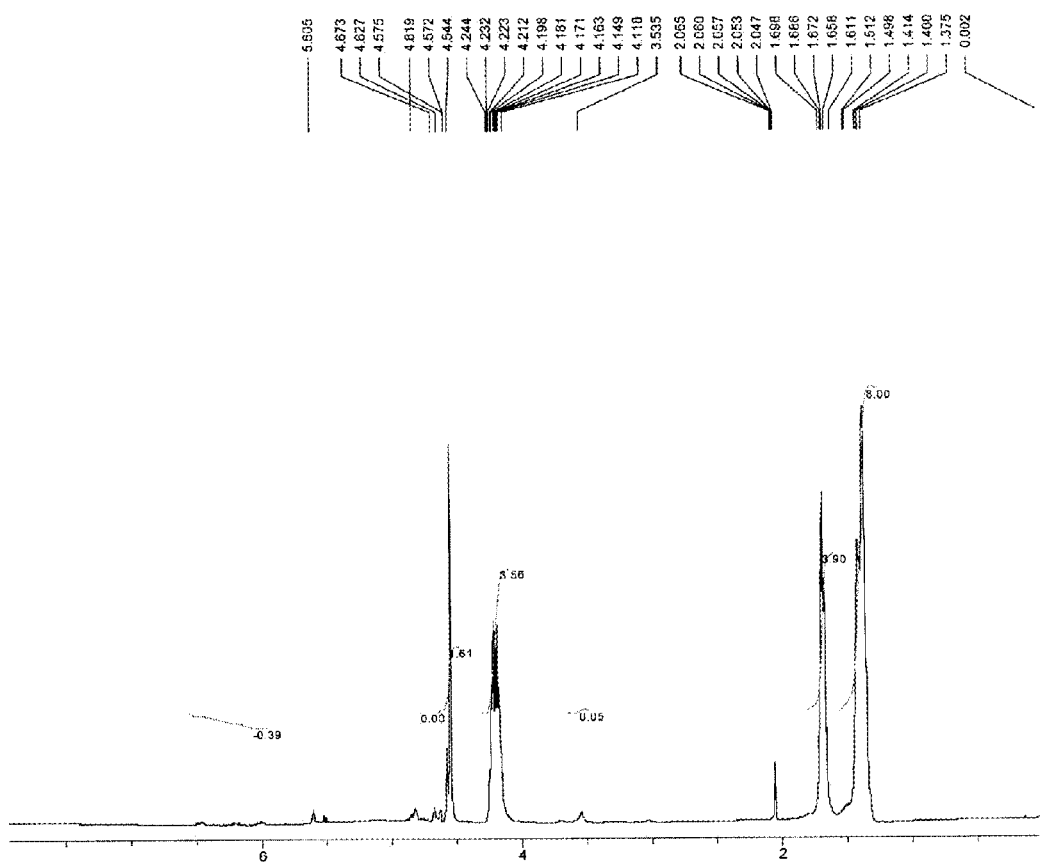
FIG. 13 is a $^1$H-NMR spectrum of an acrylated condensation polymer (composed of tartaric acid and 1,8-octanediol (POT)) (1:1 acryloyl chloride:condensation polymer)

FIG. 12 shows the overlaid IR spectra of both POT and APOT using 3:1 molar ratios of ACRL:POT in which almost complete conversion took place indicated by the disappearance of OH stretching of the acrylated SCP and the formation of the terminal vinyl groups indicated by the appearance of the new C=C stretching vibration showed at around 1640 cm$^{-1}$. This analysis was further confirmed using $^1$H-NMR spectroscopy in which the vinyl group's presence is illustrated by the peaks in the region between 5.9 and 6.1 ppm as shown in FIG. 13. It is clear here that there were no interfering peaks of any kind in the $^1$H-NMR of the purified APOT compared to the non-acrylated POT.

Example 5

Figure 10:
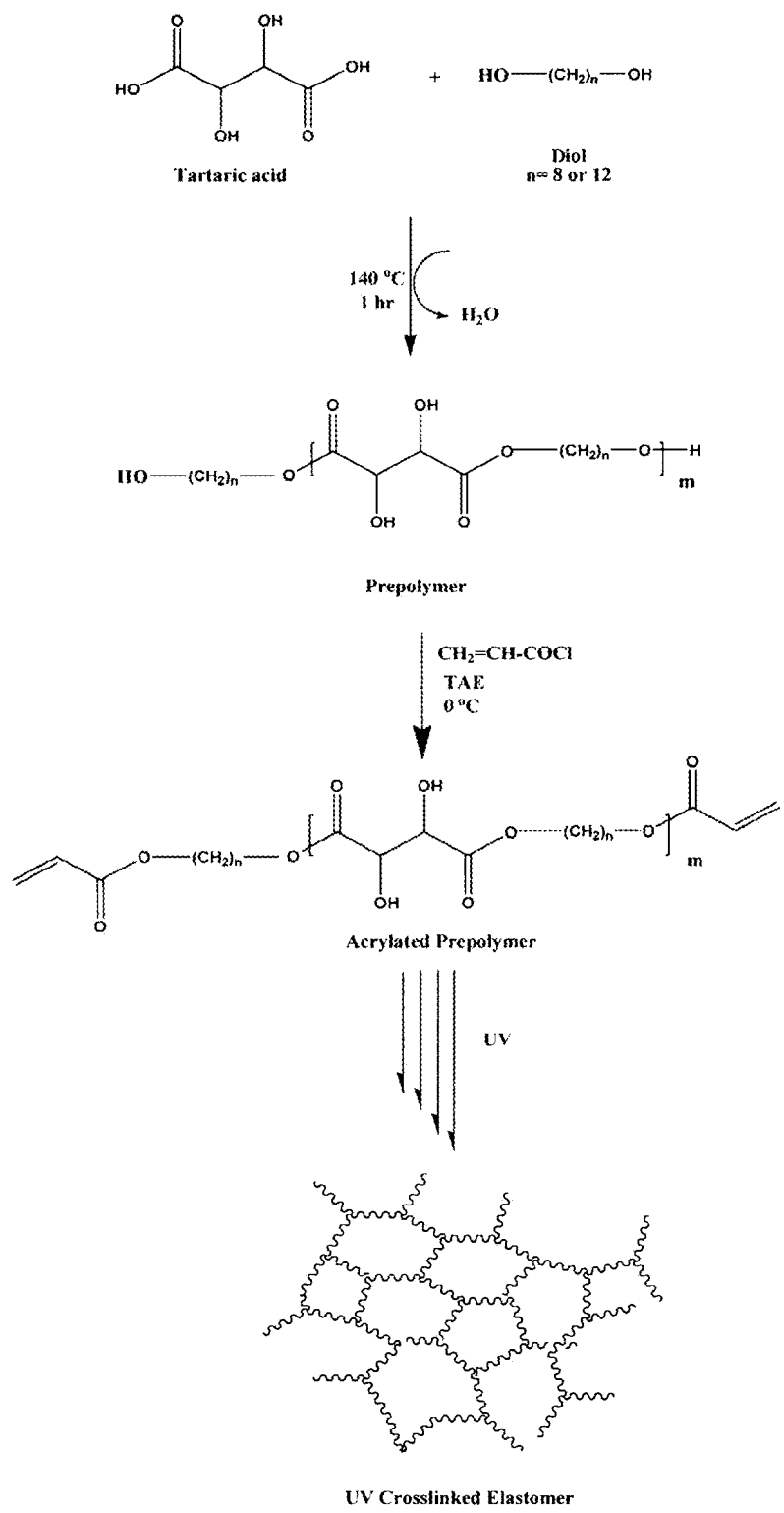
FIG. 10 shows the preparation of a biodegradable and biocompatible elastomeric polymer using tartaric acid and 1,8-octanediol to form the condensation polymer (POT) and photocrosslinked according to an embodiment of the disclosure.

UV-Crosslinking of Acrylated POT (a) Procedures:
50 µl of the UV initiator solution (30% w/v of 2,2-dimethoxy-2-phenyl-acetophenone (DMPA) in acetone) was mixed with 1 g of APOT. The mass was further mixed and then transferred into a glass mould (80×6×2 mm). The sample was then exposed to UV light at a distance of 10 cm at room temperature for 5 minutes using model B-100AP UVP high-intensity long wave inspection lamp of 21,700 µw/cm$^2$ relative intensity The successfully formed elastomer was then removed from the mould and subjected to chemical, thermal, and mechanical characterization. FIG. 10 shows the UV crosslinking process of APOT.

After preparing and purifying the set of acrylated POT condensation polymers, we attempted to undergo a UV photo-initiated radical crosslinking using 2,2-dimethoxy-2-phenyl-acetophenone (DMPA) as a photoinitiator. The latter possess some advantages that make it preferable to us over other initiators. First, it demonstrated high photoinitiation reactivity which results in accelerated UV crosslinking process. Second, its structure and free radical polymerization mechanism reduce the extractable amount of unreacted photoinitiator taken by the UV-cured polymer with no significant loss in the initiation efficiency[36] and finally, its reported biocompatibility.[32] Complete polymerization was achieved after 5-10 minutes exposure of the sample to LWUV light at a distance of 10 cm. This exposure time and distance was enough to achieve complete photo-crosslinking of the prepared acrylated POT. It was also noticed that once the photopolymerization process started, the formation of the crosslinked elastomer was quick and accompanied by instant evaporation and removal of the DCM traces from the photoinitiator solution.

Example 6

Loading of Pilocarpine Nitrate for Release Studies

The pure APOT condensation polymer mass was mixed with the powder of the water soluble drug, Pilocarpine Nitrate (PN) (of particle size less than 45µ and of particle size 45-106µ) to achieve 15% v/v loading. To each 1 g of the mixed mass, 50 µL of UV initiator solution (30% w/v of 2,2-dimethoxy-2-phenyl-acetophenone in acetone) was then added. The thick mass was then mixed and then transferred into tablet teflon moulds of 1 cm diameter and 0.3 cm thickness. The samples were then exposed to UV light at 10 cm distance for 5 minutes, producing tabular elastomers ready for the release study.

Example 7

In Vitro Release Studies from APOT (a) Procedures:
The prepared monolith tablets of 15% v/v PN loading were subjected to in vitro release studies in PBS of pH 7.4 at 37° C. Triplicates were used from each of the prepared tablets (control tablets, tablets loaded with 15% v/v PN of particle size<45 µm, and tablets loaded with 15% v/v PN of particle size 45-106 µm). Each tablet was put into a capped 30 ml scintillation vial filled with 20 ml of PBS dissolution medium. The vials were placed in a rack in a Fisher brand shaking water bath adjusted at a shaking frequency of 50 and maintained at 37° C. The medium was sampled at predetermined time intervals and replaced with fresh medium to ensure the continuation of the sink condition. Samples withdrawn were filtered and the PN concentration was determined in buffer medium by UV method of analysis at a maximum wavelength of 216 nm using Milton Ray Spectronic 601 ultra violet spectrophotometer. The percentage of PN released over time for the control and each particle size loaded in the elastomers were then calculated.

In an attempt to demonstrate the osmotic release mechanism of water soluble agents from this newly synthesized photoset biodegradable elastomer, PCN was used here as a model for its moderate osmotic activity and the ease of determining its concentration in the release media using UV method of analysis. Before running the release studies, the stability of PCN in the release medium was tested by monitoring the changes in the concentration of a prepared stock solution of PCN in each of them over a period of one week. The study showed no significant changes from its initial concentration over the tested period.

Without being bound by theory, the generally accepted view of drug release from an elastomeric monolith is as follows. When the volumetric loadings of the drug are below a critical volume fraction called the percolation threshold, the drug particles will not be appreciably interconnected to each other. The drug particles located on the surface dissolve and produce an initial burst effect, accounting for between 10 to 20% of the initially loaded drug, followed by a slow release period. This slow release depends on the rate of degradation of the polymer when the polymer is degradable and/or the rate of formation of cracks and interconnected pores resulting from water imbibition into the polymer. The rate of this water imbibition is proportional to the porosity of the polymer and the osmotic activity of the loaded drug. The loading of PN was chosen to be 15% v/v as it is less than the percolation threshold in monolithic systems (20-25% v/v) and was the maximum volumetric loading that we were able to achieve without affecting the UV light penetration during the crosslinking process.

In an attempt to demonstrate the osmotic release mechanism of water soluble agents from this newly synthesized photoset biodegradable elastomer, PCN was used here as a model for its moderate osmotic activity.

Figure 14:
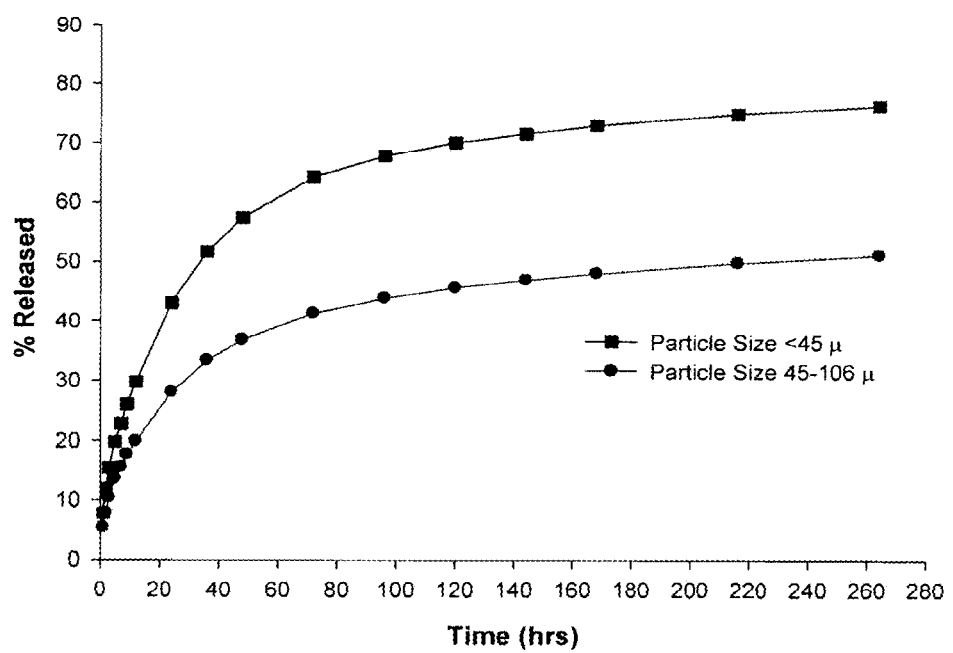
FIG. 14 is a graph showing the release of pilocarpine nitrate from UV photocrosslinked elastomeric polymer

As can be seen from FIG. 14, a large fraction of PN (30-40%) was released during the initially rapid release phase after which the release becomes constant and slower in rate. The rate of release depended on the particle size of PN powder used in loading the tablets. It is clear that although the tablets loaded with larger particle size (45-106 µL) followed the same trend of release from tablets loaded with particle size less than 45 µL, the rate of release was much slower.

Example 8

Visible Light Crosslinking of Poly(Diol-Tricarballylates)

(a) Synthesis of poly(1,8 octane diol-co-tricarballylate) (POTC) condensation polymer Into a three-neck 250 ml round-bottom flask equipped with a condenser, a nitrogen inlet and a magnetic stirrer, was added 8.77 g of 1,8 octane diol (0.06 mole), 7.05 g of tricarballylic acid (0.04 mole) and 0.16 g of stannous octoate (equivalent to 1% w/w of reactants) as a catalyst. The mixture was heated to 140° C. under continuous stirring for 20 minutes. The reaction continued for 10 more minutes under vacuum (20 inch Hg) to distill off the formed water. The resulting crude product was then purified by dissolving in acetone and precipitation in cold anhydrous ethyl ether. The condensation polymer formed was then dried under vacuum (20 inch Hg) overnight.

The following poly (diol-tricarballylate) condensation polymers were also synthesized using the same method: poly(1,6 hexane diol-co-tricarballylate) (PHTC), poly(1,8 octane diol-co-tricarballylate) (POTC), poly(1,10 decane diol-co-tricarballylate) (PDTC) and poly(1,12 dodecane diol-co-tricarballylate) (PDDTC).

(b) Acrylation of poly(1,8 octane diol-co-tricarballylate) (POTC)

Into 250 ml round-bottom flask equipped with a magnetic stirrer, 10 g of POTC was dissolved in 60 ml of acetone to which 10 mg of 4-dimethyl aminopyridine (DMAP) was added as a catalyst. The flask was sealed, flushed with argon and then immersed in a 0° C. ice bath. A stepwise addition of 2.37 ml of acryloyl chloride (2.92 mmole) with an equimolar amount of triethylamine (TEA) (4.05 ml) to the solution was performed over a period of 12 hours. The equivalent molar amount of triethylamine was used to scavenge the hydrochloric acid formed during the reaction. The reaction was continued at room temperature for another 12 hr. The reaction completion was detected using thin layer chromatographic analysis and the final solution was filtered to remove triethylamine hydrochloride salt formed during the acrylation reaction. The acrylated POTC solution was then dried at 45° C. under vacuum (25 inch Hg) using a rotary evaporator and then dissolved in chloroform. Further purification was done by washing this chloroformic solution several time with deionized water and then dried over anhydrous sodium sulphate. The chloroform was then evaporated at 45° C. under vacuum (25 inch Hg) using rotary evaporator and the acrylated POTC was left in the vacuum oven over night at room temperature for complete removal of solvent. The final purified product was then subjected to spectroscopic and thermal analysis to confirm the chemical structure and the final product's purity and thermal properties.

The acrylated PHTC, PDTC and PDDT condensation polymers were prepared following the same procedure described above but using varying reactant amounts that would achieve the preparation of condensation polymers with 100%, 75% and 50% degrees of acrylation.

(c) Visible Light Photocrosslinking of POTC

On a watch glass and under dark conditions (in dark fume hood equipped with sodium lamp), 5 µl of 10% ethanolic solution of both camphorquinone and triethanolamine (0.01% (w/w) photoinitiator) was added to 5 grams of the acrylated POTC. The mixture was then left under vacuum (25 inch Hg) for 4 hr and at 40° C. to ensure complete removal of any traces of alcohol from the photoinitiator solutions. The dried sample of the condensation polymer that was mixed with the initiator was then poured into a Teflon mould using a spatula. The mould was then exposed at room temperature to visible light using a 100 watt tungsten lamp at a distance of 10 cm for 10 minutes to form the elastomer which was then removed from the mould for further testing.

Figure 15:
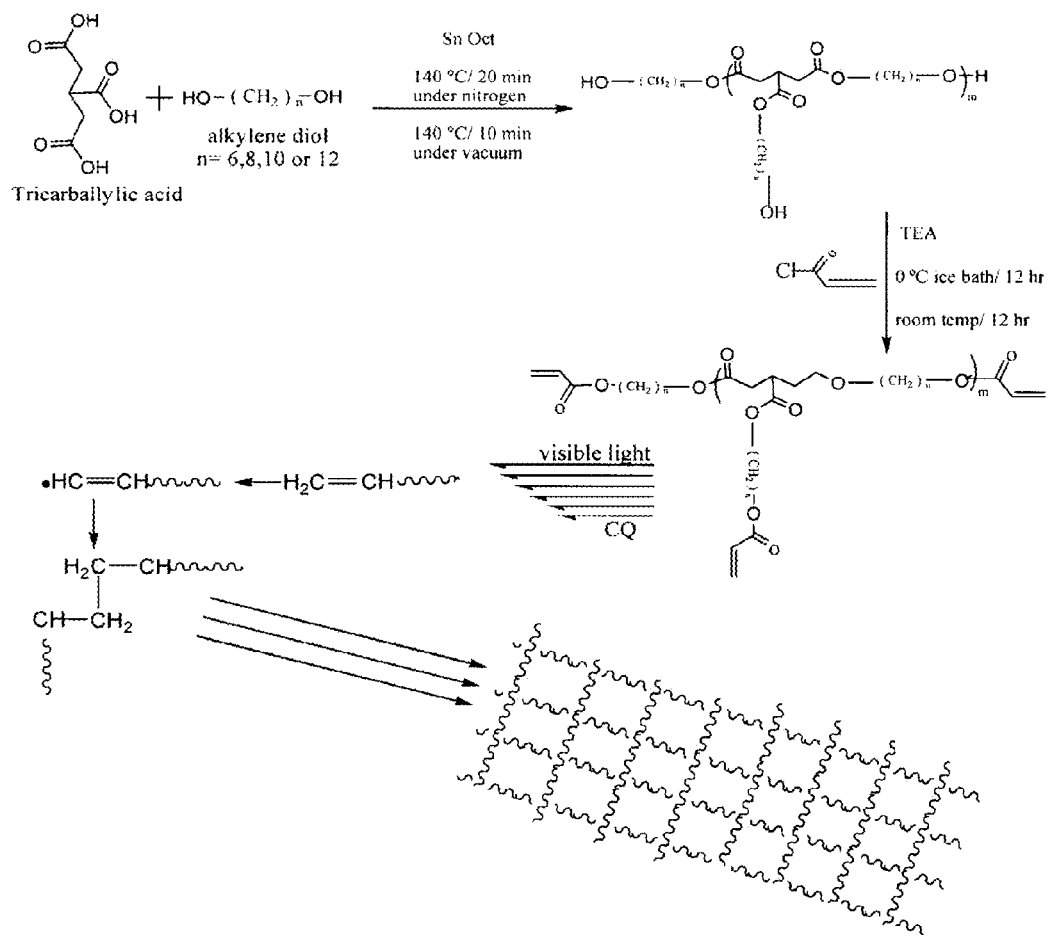
FIG. 15 shows the preparation of a biodegradable and biocompatible elastomeric polymer using tricarballylic acid and an alkylene diol to form the condensation polymer, reacted with acryloyl chloride and photocrosslinked with visible light.

Visible light photocrosslinked poly (diol-tricarballylate) elastomers were prepared in three steps as shown in FIG. 15. First, tricarballylic acid was reacted with excess diol to produce low molecular weight condensation polymers. To obtain low molecular weight condensation polymers, the reaction was stopped after 30 minutes. The obtained condensation polymers were transparent colorless viscous liquids at room temperature or were slightly yellowish in color. The second step involved the conversion of the terminal hydroxyl groups in the prepared condensation polymers network into vinyl groups by an acrylation process. The obtained acrylated condensation polymers were also transparent colorless viscous liquids or slightly yellowish in color. Both of the acrylated and unacrylated condensation polymers did not dissolve in water but were soluble in most organic solvents. In the last stage, visible light photocrosslinking of the acrylated condensation polymers were conducted which resulted in the formation of elastomeric crosslinked networks. The photocrosslinked elastomers were stretchable and rubbery and swelled but did not dissolve in organic solvents.

The molecular weights of the condensation polymers as measured via GPC are listed in Table 5. As expected, the molecular weights of the condensation polymers prepared increased upon increasing the number of methylene units in the chain length of the used diol. The GPC analysis also showed that the prepared condensation polymers demonstrated narrow distribution of their molecular weights with polydispersity indices approaching unity (1.04-1.39). Also, the results of chemically determined millimoles of terminal hydroxyl groups were listed in Table 5. The estimated numbers were similar to those obtained from GPC analysis which indicated that the polymerization proceeded as estimated. End group analysis for the prepared condensation polymers was important to determine the number of hydroxyl groups available for further acrylation reaction (extent of acrylation). In other words, the condensation polymers reacted with the optimum amount of acryloyl chloride.

Figure 16:
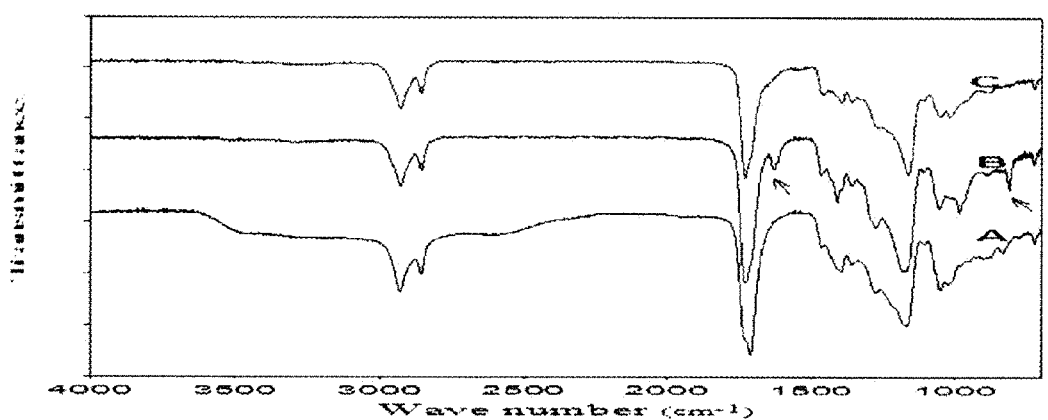
FIG. 16. is a stacked FT-IR spectrum of a condensation polymer (composed of tricarballylic acid and 1,8-octanediol (POTC)) (A), the acrylated condensation polymer (B) and the photocrosslinked elastomeric polymer.
Figure 17:
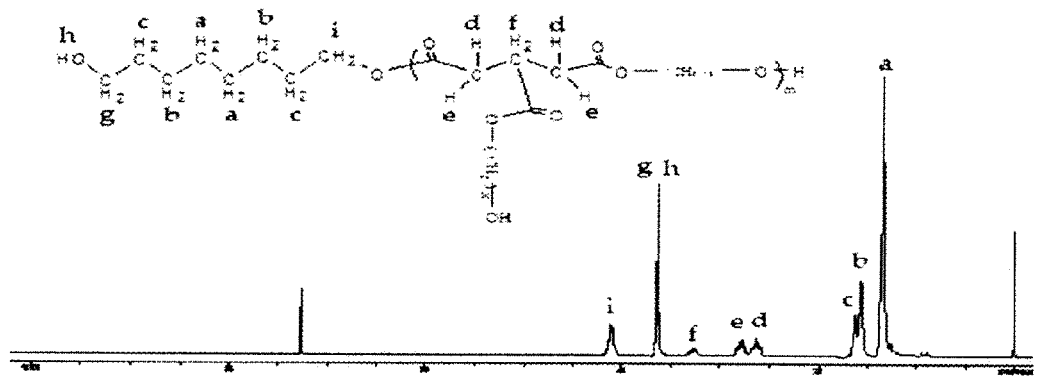
FIG. 17 shows the $^1$HNMR of condensation polymer of tricarballylic acid and 1,8-octanediol (a), and the acrylated condensation polymer (b)
Figure 17:
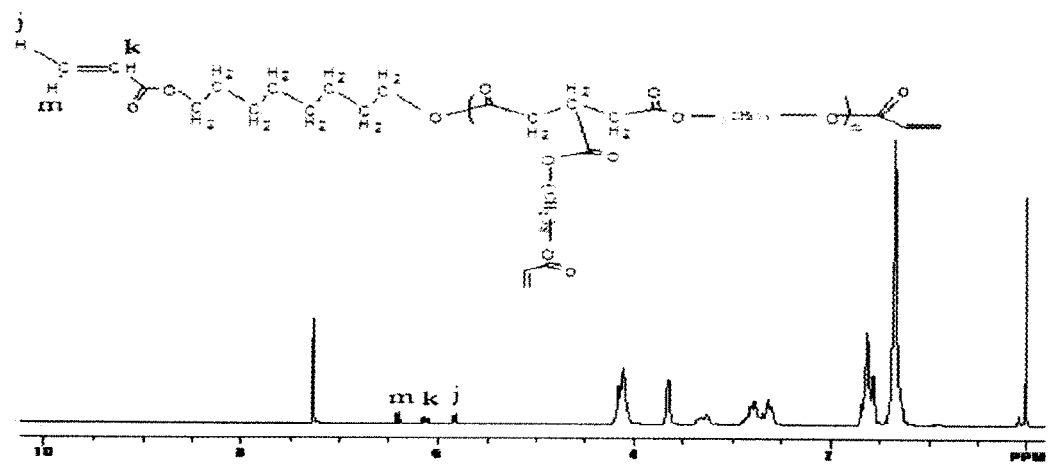

The POTC purified condensation polymer, acrylated condensation polymers and elastomer were all characterized using FT-IR analysis. As shown in FIG. 16, the IR spectrum of the purified POTC condensation polymer (FIG. 16—Spectrum A) showed a broad absorption peak at 3600-3400 $cm^{-1}$ that was attributed to hydroxyl stretching vibrations. The broadening in the peak was attributed to the intermolecular hydrogen bond formation. The absorption bands at about 2930 $cm^{-1}$ and 2857 $cm^{-1}$ were attributed to C—H stretching vibrations. The carbonyl group of the formed ester appeared at about 1710 $cm^{-1}$. The peaks from 1300-1000 $cm^{-1}$ were attributed to C—O stretching vibrations. In the acrylated spectrum (FIG. 16-Spectrum B), the disappearance of the broad OH peak and the appearance of two new peaks at around 1635 and 813 $cm^{-1}$ was indicative that the incorporation of the acrylate moieties was successfully achieved. The first peak at 1635 $cm^{-1}$ corresponds to the C=C bond stretching, while the peak at 813 $cm^{-1}$ corresponds to C=C bond twisting vibrations. These two peaks are related only to the acrylated groups and known not to be present in the FT-IR of acryloyl chloride. The same two peaks at 1635 and 813 $cm^{-1}$ completely disappeared after the photopolymerization took place (FIG. 16-Spectrum C). This was attributed to crosslinking process that consumes the C=C terminal bonds in the free radical initiated reaction. As previously illustrated in FIG. 15, a free radical is formed by the decomposition or oxidation of the photoinitiator in the presence of light. This free radical initiates abstraction of one hydrogen atom of the double bond —CH=$CH_2$ of the acryloyl moiety. The acrylated free radical then attacks a double bond in an adjacent polymer chain. This results in the formation of crosslinks and the regeneration of a free radical in a reaction analogue to propagation in an addition polymerization FIG. 17 shows the $^1$H-NMR spectrum of POTC condensation polymer and its acrylated condensation polymer. In the condensation polymers spectrum (FIG. 17a), the peaks at about 1.3 and 1.7 ppm can be attributed to the methylene protons —$CH_2$— in the aliphatic chain. The difference in their chemical shift values were due to the difference in their positions relative to the ester bond and the terminal OH group. The peaks at about 2.6 and 2.8 ppm can be assigned to the two methylene protons —$CH_2$— of the tricarballylic acid, while, the single proton —CH— was assigned to the peak at about 3.3 ppm. Both the terminal OH protons and the methylene protons of —$CH_2$— attached to the terminal OH group; appear at about 3.63 ppm as the two peaks overlap over each others. The protons of the methylene group adjacent to the ester bond were assigned to the peak at about 4.2.

FIG. 17b shows the $^1$H-NMR spectrum of acrylated POTC condensation polymer. The incorporation of the terminal acrylate groups was confirmed by the appearance of three peaks at 5.8, 6.1 and 6.4 ppm, which were attributed to the presence of vinyl group. The decrease in the integration of the overlapped peaks, which appeared at about 3.63 ppm, was due to the disappearance of the terminal OH proton.

Figure 18:
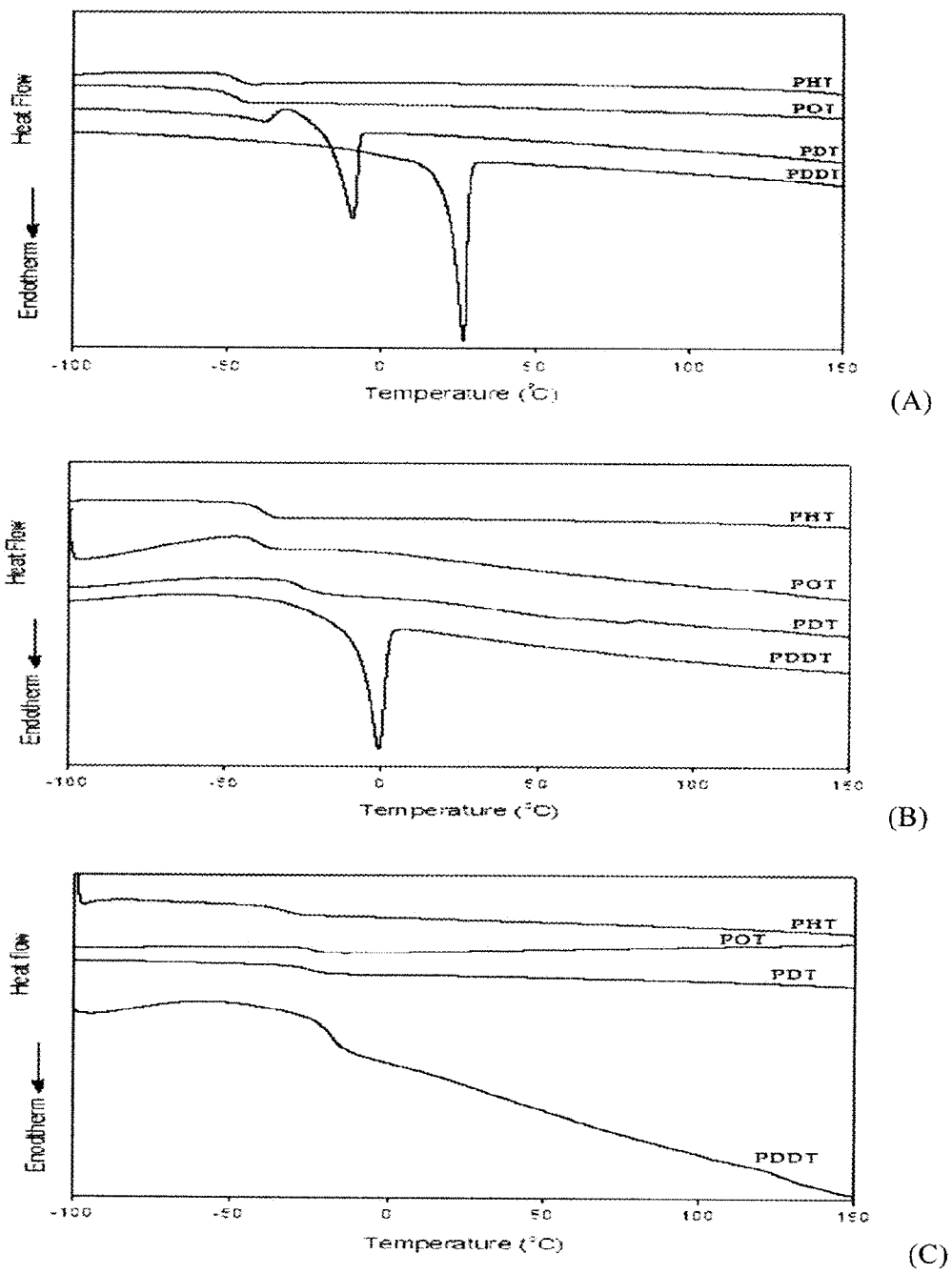
FIG. 18 shows differential scanning calorimetry thermograms, where (A) is the condensation polymer of FIG. 17, (B) is the acrylated condensation polymer of FIG. 17. and (C) is the photocrosslinked elastomeric polymer.

The thermal behaviors of the condensation polymers, acrylated condensation polymers and photocured elastomers were also examined with DSC, and the results are summarized in Table 6 and illustrated in FIG. 18. As can be seen from FIG. 18a, the thermal analysis of the condensation polymer showed that PHTC and POTC were both amorphous with glass transition temperatures ($T_g$) of −49 and −46° C., respectively. On the other hand, PDTC and PDDTC were both crystalline. PDTC showed a Tg and melting temperature ($T_m$) of 36 and −9° C., respectively. PDDTC showed a melting temperature at 26° C. and the calculated latent heat of fusion (ΔH) from its melting endotherm was 56 J/g. Following acrylation (FIG. 18b), the $T_g$ of PHTC and POTC increased. PDTC became amorphous with $T_g$ at −26° C. Finally, $T_m$ and ΔH of PDDTC decreased to 0° C. and 31 J/g, respectively. After photopolymerization (FIG. 18c), all the crosslinked elastomers were amorphous with Tg's below 37° C. which indicated that all elastomers were in a highly elastic state at body temperature.

The thermal behaviors of the condensation polymers, acrylated condensation polymers and photocured elastomers can be explained as follows: First, as the number of methylene groups in the polymer chain increases, the molecular weight will also increase resulting in an increase in both the Tg and the degree of the polymer crystallinity. This is consistent with the fact that Tg and crystallinity for an aliphatic polyester increases with an increase in the number of methylene groups in their chain length[38]. Second, the incorporation of acryloyl group at the ends of the condensation polymers led to an increase of the $T_g$ as well as a decrease in the crystallinity compared to those of the unacrylated condensation polymers. This behavior has previously been observed for some polyester elastomeric networks[39]. This change in Tg ranged from 11 to 6° C. for PHTC and POTC, respectively. It was also noted that the acrylation process diminished and decreased the crystallinity of PDTC and PDDTC, respectively. Third, crosslinking resulted in additional increase in $T_g$ and decrease in the crystallinity compared to those of the uncrosslinked acrylated condensation polymers. In particular, crystal formation of acrylated PDDTC was remarkably diminished by the photocrosslinking reaction, thus the PDDTC networks became completely amorphous. This trend is explained by the facts that crosslinking suppressed the mobility of molecular chain and prevented chain rearrangement as a result of which an obstruction of crystal formation took place[40].

After preparing and purifying the acrylated condensation polymers, we attempted to undergo visible-light crosslinking using camphorquinone and triethanolamine as a photoinitiator. Curing was achieved after 10 minutes exposure to visible light at a distance of 10 cm. Crosslinked network formation was confirmed by immersing the elastomers in acetone, the elastomers swelled but did not dissolve.

To determine the effect of chain length of the diol monomer and degree of acrylation on the mechanical properties of the crosslinked elastomers, all the prepared PHTC, POTC, PDTC, and PDDTC with different degrees of acrylation were subjected to tensile testing.

Figure 19:
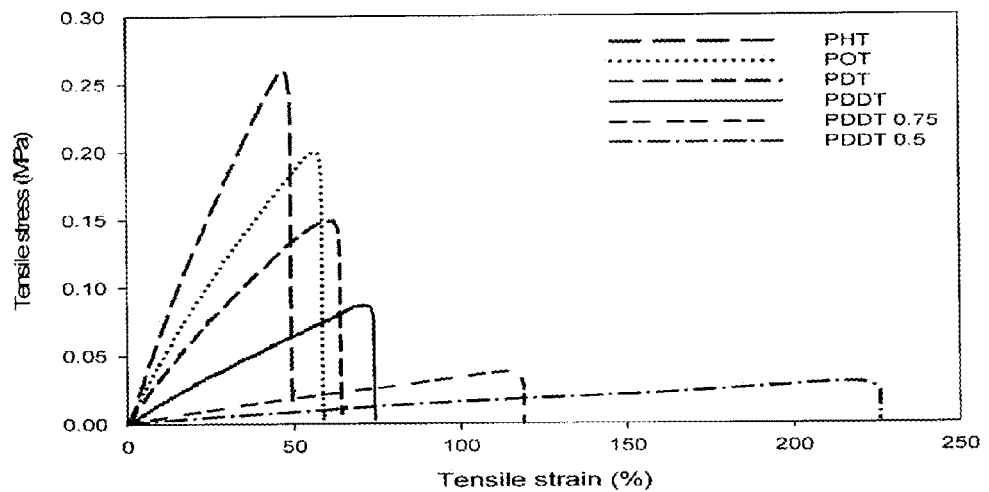
FIG. 19*a* shows the stress strain curves of photocrosslinked elastomeric polymers comprised of 1,6-hexanediol (PHTC), 1,8-octanediol (POTC), 1,10-decanediol (PDTC) and 1,12-dodecanediol (PDDTC) with tricarballylic acid according to an embodiment of the disclosure and FIG. 19(*b*) shows the mechanical testing of an elastomeric polymer.
Figure 19:
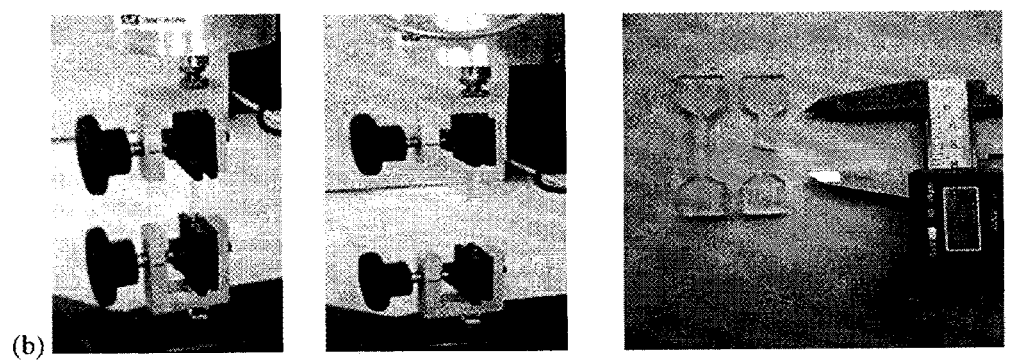

FIG. 19a shows that tensile testing of the photocrosslinked poly (diol-tricarballylate) elastomers produced representative uniaxial tensile stress-strain curves which are characteristics of typical elastomeric materials. Average values for Young's modulus (E), ultimate tensile stress (σ), cross-linking density ($\rho_x$), and maximum strain (ε) are summarized in Table 7. The mechanical properties spanned from elastic to brittle depending on the diol used and the degree of elastomer acrylation. No permanent deformation was observed during the mechanical testing (FIG. 19b), the ultimate tensile strength was as high as 0.25 MPa and the ultimate tensile strain (elongation) was as high as 238.28%, under the synthesis condition. As seen in Table 7, PHTC elastomer has the highest ultimate tensile strength and Young's modulus values. This was attributed to the fact that PHTC possessed the lowest number of methylene groups in the chain (molecular weight) of the diol used in the prepared condensation polymers. As the diol chain length of the condensation polymers decreased, the cross-linking density of the polymer increased which resulted in the formation of a crosslinked elastomer that is stiffer and less extensible. On the other hand, increase in the alkylene diol chain length decreased the crosslinking density and therefore, increased the ultimate elongation of the elastomer. Finally, It was also noted that, the decrease in the degree of acrylation of the acrylated condensation polymers resulted in a decrease in the cross-linking density which increased the elastomer stretchablility and elasticity as shown in FIG. 19a.

The mechanical properties of the photocrosslinked poly(diol-tricarballylate) elastomers, and other similar elastomers, can be controlled by altering the number of methylene groups in the chain of precursor diol or by changing the degree of acrylation. This demonstrates the potential of achieving the mechanical compliance of different tissue engineering, drug delivery and other biomedical applications requirements. For example, the rate of drug delivery of various drugs and their stability highly depend on the mechanical properties of the used elastomer as well as its rate of degradation. When the elastomer is able to maintain its 3D structure during the release period, then you are able to keep the delivery mechanism intact as this is the key for the diffusion or osmotic-driven release mechanism. Also, manipulating the mechanical properties will enables one to design an elastomer that will guarantee that the majority of pH sensitive drugs will be released before major degradation (acid accumulation) takes place. For tissue engineering, the use of elastomeric material will adapt to the mechanical challenges inside the implanted area as well respond easily to mechanical stimuli in the place of implantation. Specific applications in tissue engineering include vascular tissues and blood vessel engineering, regenerative nerve endings, skin substitute or burn dressing. Further, myocardial tissue lacks significant intrinsic regenerative capability to replace the lost cells, so elastomeric patches to replace infarcted myocardium and enhance cardiac function. As such, this elastomer can be also used to develop a biocompatible, degradable and superelastic heart patch for reconstruction of lost tissue in the heart.

Figure 20:
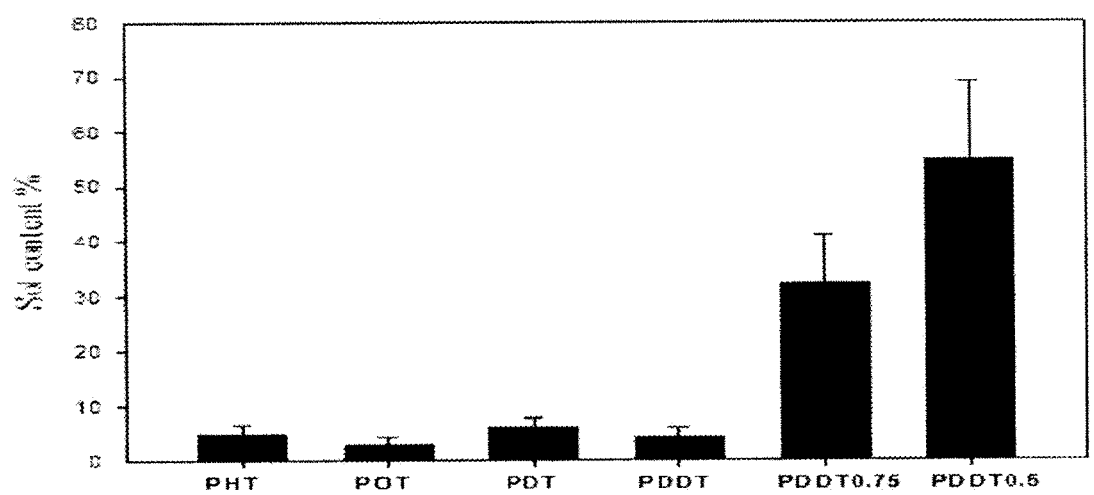
FIG. 20 is a graph showing the sol content of the elastomeric polymers of FIG. 19*a*.

FIG. 20 presents the sol-gel content for the different poly(diol-tricarballylate) elastomers. As can be seen, the chain length of the alkylene diol precursor used did not significantly affect the sol content. However, the sol content was significantly affected by varying the degree of condensation polymer acrylation. $PDDTC_{0.5}$ elastomer with 50% degree of acrylation possessed the highest sol content among all the prepared elastomers and demonstrated the highest stretchability (Table 7).

In order to examine the influence of chain length on the degradation rate and the changes in the mechanical properties of the elastomer during the in vitro degradation, four different elastomers, based on varying chain lengths of alkylene diol (C6-C12), were prepared and tested. FIGS. 21a and 21b show the weight loss and water absorption data for the four prepared elastomers. As can be seen, the water absorption and weight loss of the elastomers were directly proportional to the chain length of the alkylene diol used and inversely proportional to the elastomers crosslink density, as listed in Table 4. At the end of 12 weeks period, PHTC elastomer, which had the lowest number of methylene groups in its chain and the highest crosslinking density (14.8 mole/m$^3$), demonstrated the lowest weight loss (22%) with minimal water uptake rate (36%). On the other hand, PDDTC elastomers, which had the highest number of methylene groups in their chain and the lowest crosslinking density (87.4 mole/m$^3$), demonstrated the highest weight loss (33%) and the fastest water uptake rate (94%).

Figure 21:
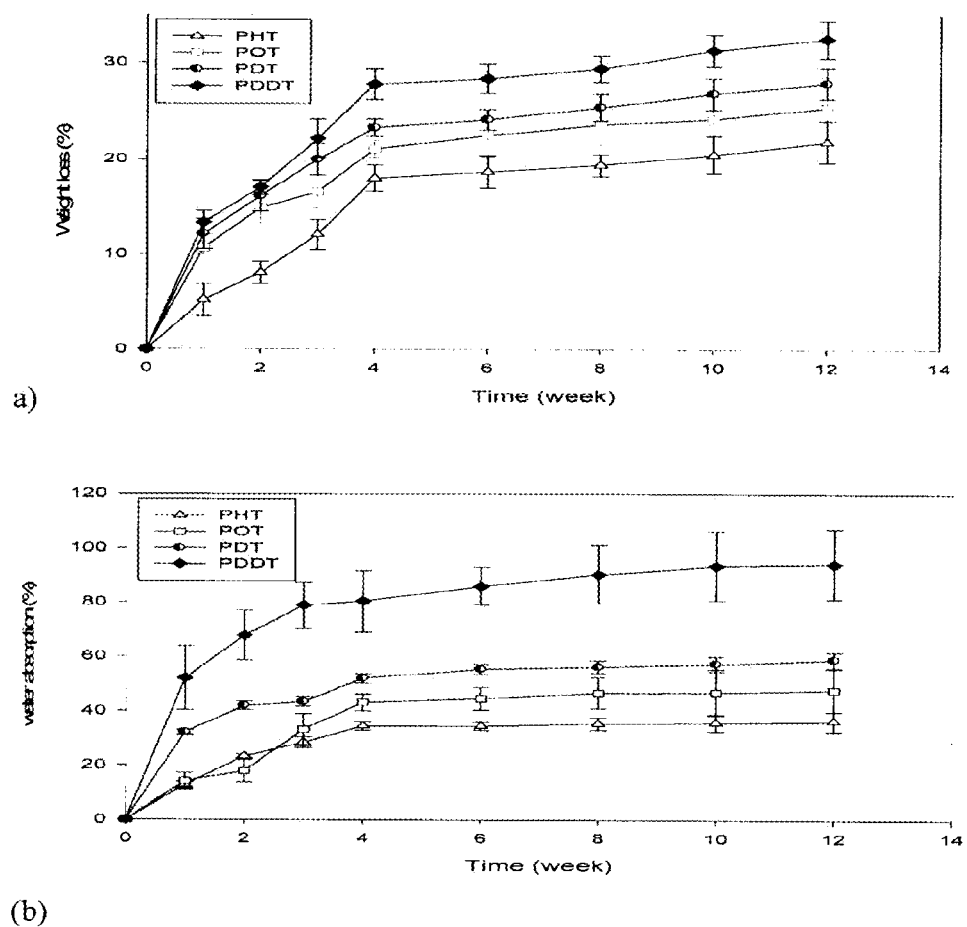
FIG. 21 shows graphs showing the degradation of elastomeric polymers of FIG. 19*a*, where (a) shows the percentage weight loss over time and (b) shows percentage water absorption over time.
Figure 22:
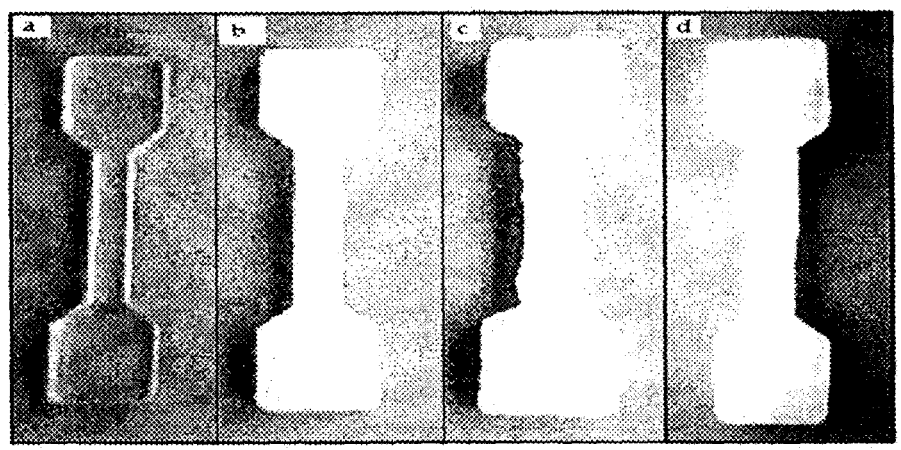
FIG. 22 shows photographs of PDDTC elastomers during in vivo degradation, where (a) is after 0 weeks, (b) 1 week, (c) 4 weeks and (d) 12 weeks.

It is well known that surface erosion occurs if hydrolysis and mass loss start without any direct correlation with water absorption. In other words, surface hydrolysis occurs when the elastomer's degradation rate is faster than the rate of water diffusion into the elastomer. In contrast, bulk erosion occurs if degradation and weight loss are correlated with the rate of water penetration into the bulk of the elastomers. As shown in FIG. 21, all the elastomers exhibited a two-stage degradation behavior. In the first stage, which lasted up to 4 weeks, the water absorption and weight loss proceeded rapidly which resulted in a significant change in elastomer's morphology (FIG. 22c). However, in the second stage, the water absorption and weight loss took place in a slower fashion and exhibited little observable changes in dimensions of the elastomer prepared (FIG. 22d).

The degradation of the elastomers proceeded as follows: after the immersion of the elastomers in the phosphate buffered saline, water diffusion and absorption into the elastomer mass took place, resulting in the hydrolysis of the polymer chains. This process is not limited to the surface but mainly taking place in the bulk of the elastomer. This initial bulk hydrolysis resulted in the formation of oligo carboxylic acids within the polymer mass which auto-catalyzed the degradation rate further and increased the hydrophilic character of the polymer due to the formation of free —COOH and —OH moieties within the elastomer bulk. As such, the elastomers became more susceptible to absorb water, and therefore swelling in the matrix and change in elastomers from flat shape to a bloated convex shape occurred. In addition, the surface became smooth and translucent (FIG. 22c). Mass losses were also taking place in parallel with that of water absorption behavior. At the end of the first 4 weeks period, the rate of production of short chain fragments decreased significantly which resulted in a much lower internal pressure or driving force that enables those fragments to diffuse into the surrounding medium. As a result of that, the weight loss in the tested samples proceeded in a much slower fashion after the initial 4 weeks period.

In summary, the elastomers' degradation proceeded in three main stages: First, water diffused into the matrix bulk. The rate of water diffusion was mainly dependent on the elastomer's crosslink density and the chain length of the diol used in its preparation. Second, random scission of ester linkages located exclusively in the backbone took place. Finally, this scission of ester linkages resulted in mass loss through diffusion of the degradation products into the surrounding medium.

Figure 23:
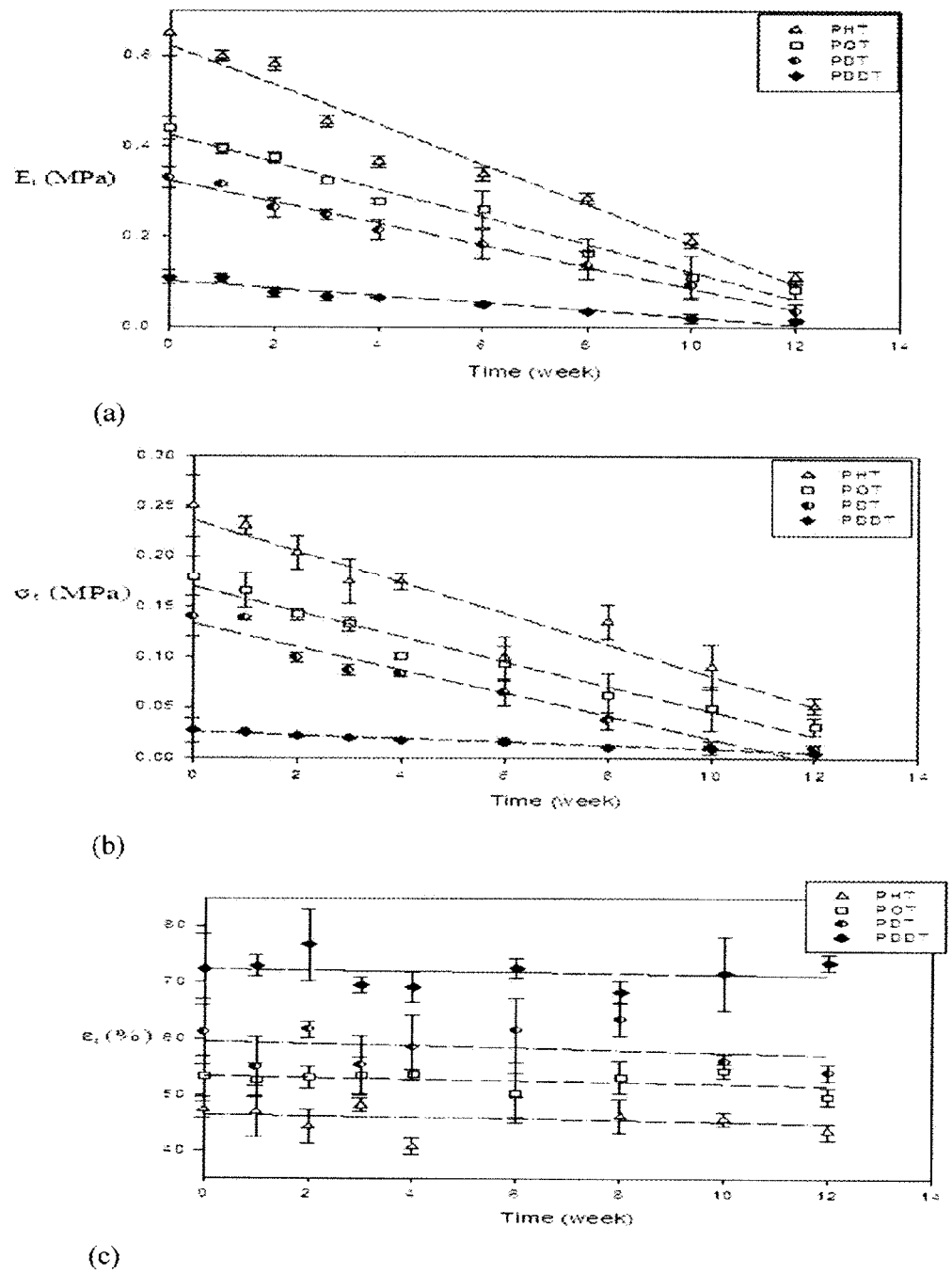
FIG. 23 are graphs showing change in tensile properties of elastomers of FIG. 19*a*, where (a) shows Young's modulus, (b) shows ultimate stress and (c) shows ultimate strain.

FIG. 23 shows the changes in the mechanical properties of the elastomers with respect to time during the in vitro hydrolytic degradations. Although the elastomers showed decrease in their mechanical strength with time, they maintained their shape and extensibility over the testing period. Young's modulus (E) and the ultimate tensile stress (σ) decreased in a nearly linear fashion with time as indicative of zero-order degradation mechanism. This linear decrease was observed regardless of the network compositions, the crosslinking density and the initial E and σ of the elastomers. FIG. 23c shows that the change in ultimate elongation (ε) was less sensitive to the degradation of those elastomers. No significant change in the ultimate elongation was found up to 12 weeks of the in vitro degradation time. These results confirmed that the hydrolytic degradation of these elastomers followed a bulk erosion mechanism, resembling the behavior of biodegradable polyesters reported in our previous studies[6]. It is only with surface erosion degradation pattern that the elastomers can maintain their mechanical properties unchanged[41]. Additionally, FIGS. 23a and 17b, shows that E and σ for all the elastomers linearly decreased with time. For example, in the first 4 weeks, PHT showed a decrease in its E from 0.65 to 0.36 MPa following a rate change of 0.07 MPa/week. On the other hand, its σ decreased from 0.25 to 0.17 MPa following a rate of 0.02 MPa/week However, after the 4 weeks period, the same elastomer demonstrated slower rates in E (from 0.36 to 0.11 MPa with a rate 0.03 of MPa/week) and σ (from 0.17 to 0.05 MPa with a rate of 0.015 MPa/week). The above observations illustrates that the changes in the mechanical properties of these networks took place in two stages. The first stage was characterized by a rapid mechanical weakening (rapid decrease in E and a) which lasted for up to 4 weeks. The second stage, which started after 4 weeks, showed a slower rate of loss in their mechanical properties. This is in correlation with the trend noted for the weight loss and water absorption reported above (FIG. 21).

Through a linear regression of the zero-order degradation kinetics of the data in FIGS. 23a and 23b using equations (1) & (2), the rate constants were calculated and are listed in Table 1.

$$E_t = E_0 - K_E t. \quad (1)$$

$$\sigma_t = \sigma_0 - K_\sigma t. \quad (2)$$

In equations 1 & 2, t denoted the immersion time (in weeks) in PBS. The values of $E_0$ and $\sigma_0$ corresponded to the intercepts obtained from extrapolating the zero-order fitted line. $K_\sigma$ and $K_E$ represented the zero-order degradation constants for Young's modulus and the ultimate tensile stress, respectively.

The decrease in the alkylene diol chain length in the elastomer was accompanied by an increase in $K_E$ and $K_\sigma$. As seen, the $K_E$ and $K_\sigma$ for PHTC were 0.0441 and 0.0154 MPa/week, respectively, while $K_E$ and $K_\sigma$ for PDDTC were 0.0080 and 0.0018 MPa/week, respectively. It was reported that Young's modulus of the elastomers depended mainly on the crosslinking density. The ultimate tensile stress depended on the distribution of end to end distances between crosslink points within the matrix.[6]

Figure 24:
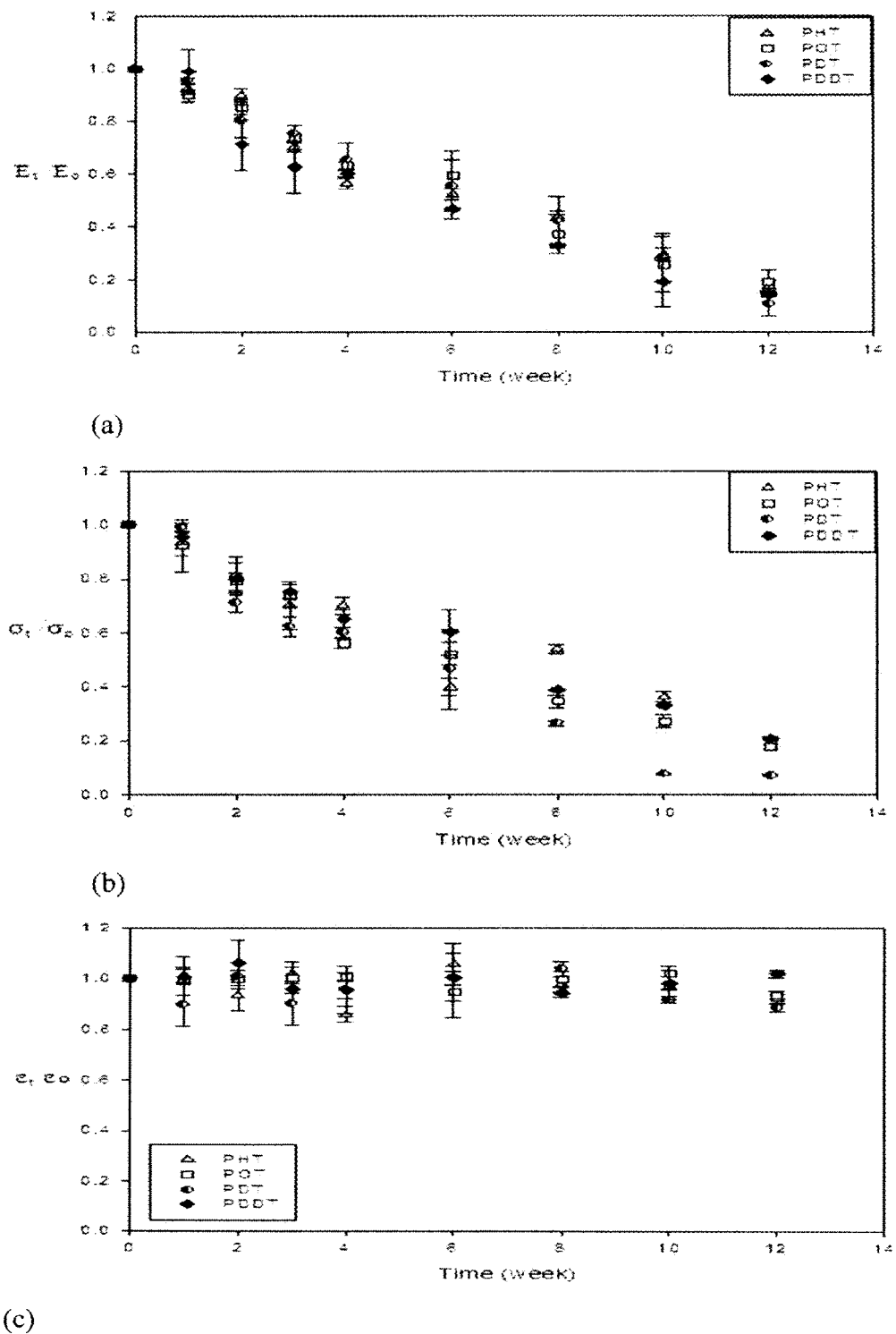
FIG. 24 are graphs showing relative change in tensile properties of elastomers of FIG. 19*a*, where (a) shows Young's modulus, (b) shows ultimate stress and (c) shows ultimate strain.

At the end of 12 weeks study period in PBS, the degradation study was stopped. At that stage, the elastomers maintained their original shape and did not degrade completely. However, the elastomers were very weak to the extent that accurate measurement of the samples tensile properties became impractical. FIG. 24 represents the normalized (value at time t divided by value at time 0) Young's modulus, the ultimate tensile stress and the ultimate elongation. These curves mirror the changes in the mechanical properties of the elastomers with respect to time during the in vitro hydrolytic degradations.

Example 7

In Vitro Biocompatibility with Fibroblast Cell

Primary human fibroblast cells were cultured in 75 ml polystyrene tissue culture plate using high-glucose Dulbecco's minimal essential medium (DMEM) supplemented with 10% (v/v) fetal bovine serum at 37° C. The fibroblast cells were plated on 24-well plates (Fischer scientific). After seeding, the cells were allowed to attach and grow and proliferate in an incubator at 37° C. Photocured poly (diol-tricarballylate) films were prepared by visible-light polymerization on glass slides. The produced films of an average dimension of 0.5×0.5 cm and with an average weight of 100 mg were cut into pieces. The pieces were added to the cells and incubated for 24 hr at 37° C. Cell density after 24 hr of incubation was assessed spectrophotometrically and then stained using phenol red dye. The cell attachment and growth using the four different poly (diol-tricarballylate) elastomeric films were compared to the control. Results reported were averages from three measurements. Phase contrast images were taken using a microscope equipped with digital camera.

Figure 25:
FIG. 25 are phase contrast images of human fibroblast cells with different elastomeric polymers.
Figure 25:
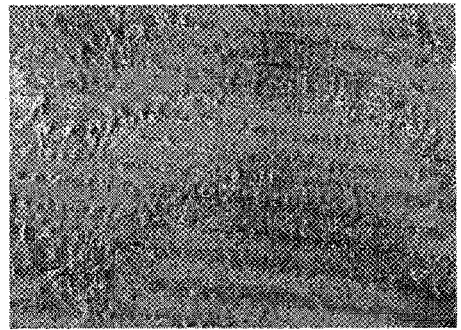
Figure 25:
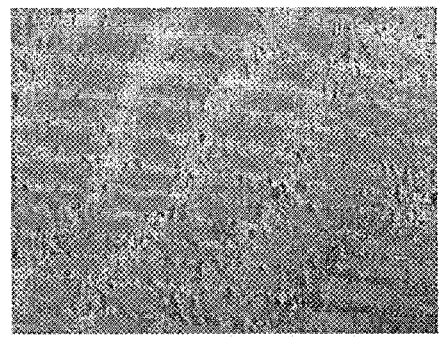
Figure 25:
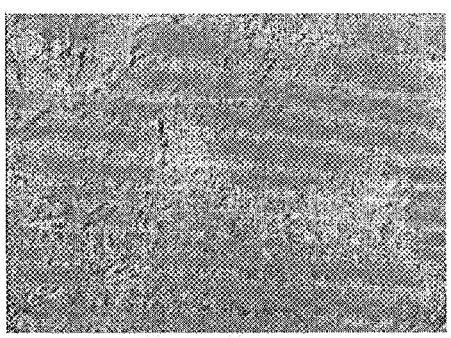
Figure 25:
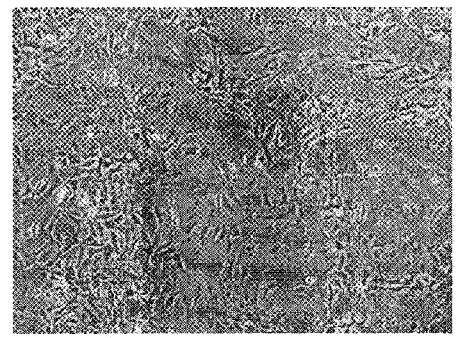
Figure 26:
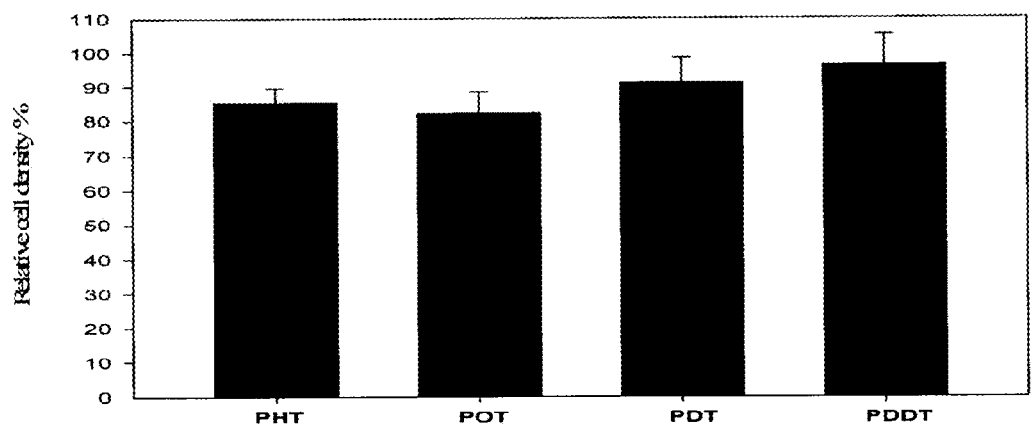
FIG. 26 is a bar graph showing the density of human fibroblast cells with different polymeric elastomers.

All the visible light photocrosslinked films were sterilized by standard autoclaving and the sterilized films were tested using a primary human fibroblast cell line. After 24 hr of culturing, fibroblast cells were found to grow with cell organization and morphology resembling that on the control polystyrene tissue culture plate (FIG. 25). The densities of these cells were measured spectrophotometrically and then compared to the densities of cells obtained from the control polystyrene plate, which was set at 100% (FIG. 26). All the measured densities were found to be nearly similar to those of the control (83-96%). The above results showed that these crosslinked elastomers were biocompatible and are useful biomaterial for controlled drug delivery and for other tissue engineering applications. For example, the rate of drug delivery of various drugs and their stability highly depend on the mechanical properties of the used elastomer as well as its rate of degradation. When the elastomer is able to maintain its 3D structure during the release period, then you are able to keep the delivery mechanism intact as this is the key for the diffusion or osmotic-driven release mechanism. Also, manipulating the mechanical properties will enables one to design an elastomer that will guarantee that the majority of pH sensitive drugs will be released before major degradation (acid accumulation) takes place. For tissue engineering, the use of elastomeric material will adapt to the mechanical challenges inside the implanted area as well respond easily to mechanical stimuli in the place of implantation. Specific applications in tissue engineering include vascular tissues and blood vessel engineering, regenerative nerve endings, skin substitute or burn dressing. Further, myocardial tissue lacks significant intrinsic regenerative capability to replace the lost cells, so elastomeric patches to replace infarcted myocardium and enhance cardiac function. As such, this elastomer can be also used to develop a biocompatible, degradable and superelastic heart patch for reconstruction of lost tissue in the heart.

Example 10

In Vitro Release of Endostatin from UV-Crosslinked APOT (a) Lypholization of Endostatin with Osmotic Excipients Recombinant Human Endostatin (rhEND) was co-lyophilized with an equivalent amount of 1:1 mixture of BSA and trehalose using succinate buffer adjusted at pH of 5.5. The excipients were added as solid fine powders to aliquots of the protein solution and stirred gently at room temperature until dissolution was complete. The solution was then filtered with a 0.22 µm low protein binding filter to remove any particulate matter. The filtered solution was subjected to a cycle of freeze drying at −48° C. and 36×10$^{-3}$ mbar for 36 hours to obtain the lyophilized mix. The lyophilized product was then ground into powder using a mortar and pestle and sieved through a 220 µm to 300 µm mesh sieve.

(b) Preparation of Endostatin Loaded Elastomeric Slabs

The lyophilized powder was then mixed with the APOT (0.25 g) and 12.5 µl of 2,2-dimethoxy-2-phenyl-acetophenone (30% w/v in acetone) as the photoinitiator. This mixed mass was then transferred into Teflon rectangular moulds (6 mm×5 mm×1.5 mm) which were exposed to UV lamp at a distance of 10 cm for 5 minutes to form the elastomeric crosslinked slab. After crosslinking, the drug loaded slabs were removed from the moulds and dried in the fume hood overnight. The drug content in each elastomeric slab was calculated based on 10% w/w (corresponding to an approximate 14% v/v) to ensure that the protein loading was well below the polymer percolation threshold of 30-35%. Each elastomeric matrix contained a final loading of approximately 500 ng of rhEND.

(c) In Vitro Release Studies Using rhEND

The prepared monolith slabs loaded with lyophilized rhEND were subjected to in vitro release studies using sterile PBS of pH 7.4 as a release medium. Each of the triplicate samples was put into a 4 ml scintillation vials filled with 2 ml of the dissolution medium. The vials were attached to a Glas-Col rugged culture rotator. The rotator was set at 30% rotation speed and placed in an oven at 37° C. The receptor release medium was replaced with fresh medium every sampling time to ensure sink conditions and constant osmotic pressure driving force. Solutions collected were divided into aliquots, frozen at −80° C. for subsequent analysis using ELISA system for rhEND detection.

Figure 27:
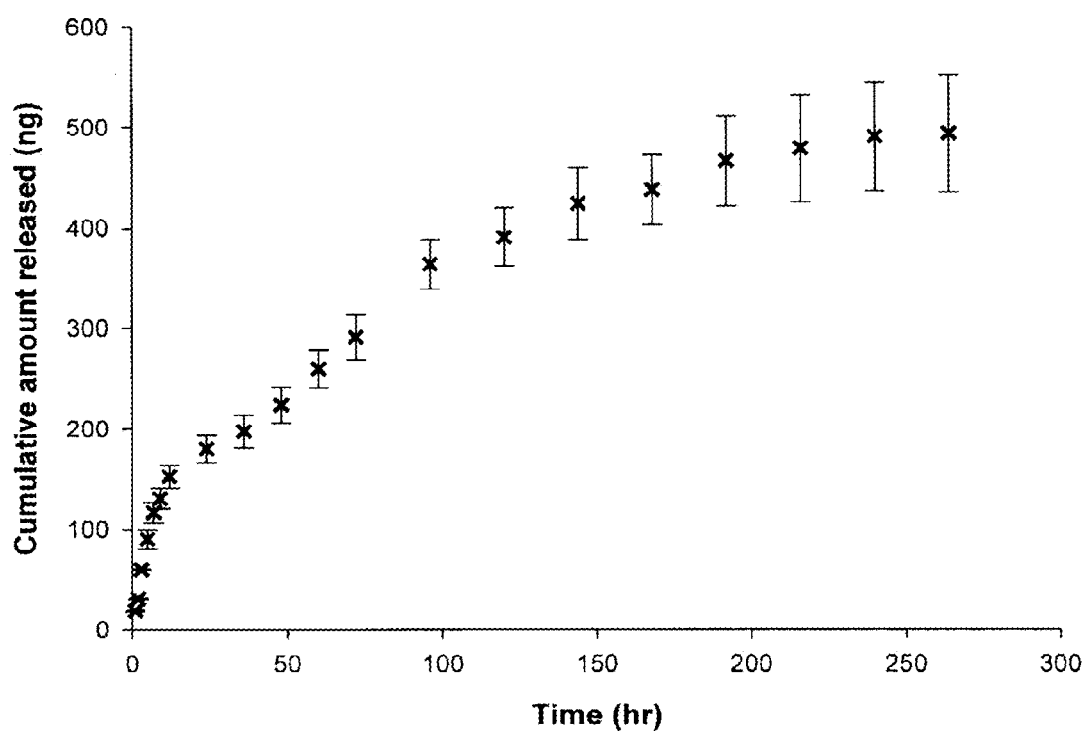
FIG. 27 is a graph showing the amount of recombinant human endostatin (rhEND) released from an acrylated condensation polymer.

As seen in FIG. 27, the release profile for rhEND consists of three distinctive phases. The initial burst release segment occurred during the first 9 hours of the release study and accounted for almost 25% of the release of rhEND. This initial phase was followed by a slower, linear, constant, and sustained release for 8 days and accounted for an additional 68% of the release of the drug. Finally, the last release segment of the profile was attributed to a mixed osmotic and polymer degradation release mechanism and was extended for another week.

Example 8

Preparation of Small-Diameter Tubular Vascular Grafts

In a dry silanized glass ampoule, 1 g of BCP was left in the preheated oven for 5-10 minutes to melt at 160° C. A molten mass of 4 g condensation polymer (POT) and SnOct equivalent to 1.4×10$^{-4}$ mol for each 1 mol of the monomer was added to the ampoule. Sodium Chloride powder (amount and particle size depends on degree of porosity and size of pores needed) was also added and the content was mixed using a vortex mixer. The ampoule was sealed under vacuum and was left in the vacuum oven at 120° C. for 1 hour. The seal was broken and the highly viscous liquid was cast on the surface of micro cylindrical Teflon molds. The molds coated with the condensation polymer was transferred into a vacuum oven and crosslinked at 120° C. for 18 hours. Sodium chloride in the resulting tubular grafts was leached out by successive incubation in water for 24 hours. The final tubular scaffold was then subjected to freeze drying for 24 hours to dry it from water and then stored in dry compartment.

In a like manner, metallic biomedical devices are casted with the condensation polymer to be further crosslinked either thermally or by UV forming a coat around the device. Thus, the present disclosure includes a method of coating metallic biomedical devices comprising dipping the metallic biomedical device into a solution of a condensation polymer and either thermally crosslinking or photocrosslinking the condensation polymer to form a coating of a biodegradable and biocompatible elastomeric polymer over the metallic biomedical device. The coating of stents and catheters with elastic biodegradable polymer will reduce the immune reaction against the metallic object once implanted in the body. Therefore, it is a way of decreasing the immune response against the stent. Furthermore, a medical device can be coated with a biodegradable polymer loaded with a therapeutic agent in a manner suitable to expose tissue near the implantation site of the medical device to the therapeutic agent over a desired time interval.

While the present disclosure has been described with reference to what are presently considered to be the preferred examples, it is to be understood that the disclosure is not limited to the disclosed examples. To the contrary, the disclosure is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety. Where a term in the present application is found to be defined differently in a document incorporated herein by reference, the definition provided herein is to serve as the definition for the term.

TABLE 1

Ratios of POT and BCP used in the preparation of elastomers.

| Sample | ID | Condensation polymer (POT) (g) | BCP (g) | BCP/POT Weight Ratio | BCP/POT Molar Ratio |
|---|---|---|---|---|---|
| Elastomer 1 | Elast 1 | 4.0 | 1.00 | 1.00/4.00 | 1.16 |
| Elastomer 2 | Elast 2 | 4.0 | 0.75 | 1.00/5.33 | 0.87 |
| Elastomer 3 | Elast 3 | 4.0 | 0.50 | 1.00/8.00 | 0.58 |
| Elastomer 4 | Elast 4 | 4.0 | 0.25 | 1.00/16.00 | 0.29 |

TABLE 2

Glass transition temperatures of the prepared elastomers.

| Elastomer | Tg (° C.) |
|---|---|
| Elast 1 | −4.8 |
| Elast 2 | −6.1 |
| Elast 3 | −8.5 |
| Elast 4 | −9.3 |

TABLE 3

Sol Content and degree of swelling of different elastomers.

| Elastomer | Sol content % (Q) | Swelling degree (R) |
|---|---|---|
| Elast 1 | 2.16 | 161 |
| Elast 2 | 3.29 | 181 |
| Elast 3 | 6.59 | 249 |
| Elast 4 | 9.76 | 264 |

TABLE 4

Summary of the initial mechanical properties of the elastomers.

| Elastomer | E (Mpa) | σ (MPa) | ε % | ($\lambda_b$) |
|---|---|---|---|---|
| Elast 1 | 1.86 ± 0.10 | 2.99 ± 0.23 | 66.62 ± 14 | 1.34 |
| Elast 2 | 0.94 ± 0.09 | 1.95 ± 0.15 | 80.85 ± 18 | 1.46 |
| Elast 3 | 0.65 ± 0.07 | 1.48 ± 0.09 | 84.03 ± 21 | 1.78 |
| Elast 4 | 0.52 ± 0.05 | 1.05 ± 012 | 95.27 ± 29 | 2.04 |

TABLE 5

Gel permeation chromatography end group analysis results of poly (diol-tricarballylate) polymers

| Condensation Polymer | $M_n$ | $M_w$ | $M_w/M_n$ | GPC estimated OH (mmol/g) | Chemically determined OH (mmol/g) |
|---|---|---|---|---|---|
| PHT | 667 | 694 | 1.04 | 2.89 | 2.70 |
| POT | 934 | 1131 | 1.21 | 2.67 | 2.90 |
| PDT | 1090 | 1366 | 1.25 | 2.80 | 2.90 |
| PDDT | 1332 | 1863 | 1.39 | 2.06 | 2.20 |

TABLE 6

Thermal properties and sol content of poly (diol-tricarballylate) condensation polymers, acrylated condensation polymers and elastomers

| | Condensation Prepolymer | | | Acrylated condensation polymer | | | Elastomer |
|---|---|---|---|---|---|---|---|
| | $T_g$ (° C.) | $T_m$ (° C.) | ΔH(J/g) | $T_g$ (° C.) | $T_m$ (° C.) | ΔH(J/g) | $T_g$ (° C.) |
| PHT | −49 | — | — | −38 | — | — | −32 |
| POT | −46 | — | — | −40 | — | — | −25 |
| PDT | −36 | −9 | 32 | −26 | — | — | −24 |
| PDDT | — | 26 | 55 | — | 0 | 31 | −19 |

TABLE 7

Mechanical properties and sol content of poly (diol-tricarballylate) (PDTC) elastomers

| Elastomer | The ultimate tensile strength (σ) MPa | The ultimate elongation % (ε) | Young's modulus (E) MPa | Crosslinking density ($\rho_x$) (mole/m$^3$) | The sol content (S) % | Description |
|---|---|---|---|---|---|---|
| PHTC | 0.25 ± 0.03 | 47.36 ± 1.39 | 0.65 ± 0.05 | 87.44 ± 6.72 | 4.92 ± 1.6 | Hard, Brittle |
| POTC | 0.18 ± 0.02 | 53.30 ± 3.6 | 0.44 ± 0.025 | 59.19 ± 3.36 | 3.02 ± 1.31 | Hard, Brittle |
| PDTC | 0.14 ± 0.02 | 61.23 ± 5.83 | 0.33 ± 0.023 | 44.39 ± 3.09 | 5.95 ± 1.69 | Tough, Brittle |
| PDDTC | 0.072 ± 0.012 | 72.35 ± 6.4 | 0.11 ± 0.016 | 14.79 ± 2.15 | 4.27 ± 1.80 | Tough, Elastic |
| PDDTC$_{0.75}$ | 0.036 ± 0.002 | 121.28 ± 2.14 | 0.029 ± 0.001 | 3.9 ± 0.13 | 32.1 ± 8.78 | Weak, Elastic |
| PDDTC$_{0.5}$ | 0.029 ± 0.002 | 238.28 ± 6.11 | 0.012 ± 0.002 | 1.6 ± 0.26 | 54.6 ± 14.32 | Very weak, Elastic |

TABLE 8

Linear regression coefficients values for PDTC elastomers during in vitro degradation in PBS (pH 7.4)

| | Crosslinking density ($\rho_x$) (mole/m$^3$) | $E_0$ (MPa) | $K_E$ (MPa/week) | $\sigma_0$ (MPa) | $K_\sigma$ (MPa/week) |
|---|---|---|---|---|---|
| PHTC | 87.44 | 0.6237 | 0.0441 | 0.2359 | 0.0154 |
| POTC | 59.19 | 0.4244 | 0.0301 | 0.1697 | 0.0124 |
| PDTC | 44.39 | 0.3239 | 0.0237 | 0.1331 | 0.0114 |
| PDDTC | 14.79 | 0.1026 | 0.0080 | 0.0261 | 0.0018 |

FULL CITATIONS FOR DOCUMENTS REFERRED TO IN THE SPECIFICATION

1. Hiljanen-Vainio M, Karjalainen T, Seppala J. 1996. Biodegradable lactone copolymers. I. Characterization and mechanical behavior of -caprolactone and lactide copolymers. J Appl Polym Sci v 59: 1281-1288.
2. Schindler A, Hibionada Y M, Pitt C G. 1982. Aliphatic Polyesters. III. Molecular Weight and Molecular Weight Distribution in Alcohol-Initiated Polymerizations of epsilon-Caprolactone. Journal of Polymer Science: Polymer Chemistry Edition 20: 319-326.
3. Nijenhuis A J, Grijpma D W, Pennings A J. 1996. Crosslinked poly(L-lactide) and poly(ε -caprolactone). Polymer 37: 2783-2791.
4. Storey R F, Hickey T P. 1994. Degradable polyurethane networks based on D,L-lactide, glycolide, epsilon-caprolactone, and trimethylene carbonate homopolyester and copolyester triols. Polymer v 35: 830-838.
5. Storey R F, Warren S C, Allison C J, Puckett A D. 1997. Methacrylate-encapped poly(d,l-lactide-co-trimethylene carbonate) oligomers. Network formation by thermal free-radical curing. Polymer 38: 6295-6301.

6. Younes H M, Bravo-Grimaldo E, Amsden B G. 2004. Synthesis, characterization and in vitro degradation of a biodegradable elastomer. Biomaterials 25: 5261-5269.
7. Hiljanen-Vainio M P, Orava P A, Seppala J V. 1997. Properties of epsilon-caprolactone/DL-lactide (epsilon-CL/DL-LA) copolymers with a minor epsilon-CL content. Journal of Biomedical Materials Research 34: 39-46.
8. Joziasse C A P, Veenstra H, Top M D C, Grijpma D W, Pennings A J. 1998. Rubber toughened linear and star-shaped poly(d,l-lactide-co-glycolide): Synthesis, properties and in vitro degradation. Polymer 39: 467-473.
9. Kim S H, Han Y-K, Kim Y H, Hong S I. 1992. Multifunctional initiation of lactide polymerization by stannous octoate/pentaerythritol. Makromol Chem 193: 1623-1631.
10. Lang M, Wong R P, Chu C-C. 2002. Synthesis and structural analysis of functionalized poly(-caprolactone)-based three-arm star polymers. J Polym Sci Part A: Polym Chem 40: 1127-1141.
11. Bruin P, Veenstra G J, Nijenhuis A J, Pennings A J. 1988. Design and synthesis of biodegradable poly(ester-urethane) elastomer networks composed of non-toxic building blocks. Makromol Chem, Rapid Commun v 9: 589-594.
12. Starcher, P. S. 1963. Bis-epsilon-caprolactone. U.S. Pat. No. 3,072,680
13. Andronova N, Srivastava R K, Albertsson A C. 2005. Potential tissue implants from the networks based on 1,5-dioxepan-2-one and ε -caprolactone. Polymer 46: 6746-6755.
14. Pitt, C. G. and Schindler, A. 1983. Biodegradable polymers of lactones. U.S. Pat. No. 4,379,138
15. Schindler, A. and Pitt, C. G. Biodegradable Elastomeric Polyesters. Polymer Preprints, Division of Polymer Chemistry, American Chemical Society: Papers Presented at the Kansas City Meeting. 23[2], 111-112. 1982. Kansas City, Mo., USA, ACS, Div of Polym Chem, Washington, D.C., USA. Polymer Preprints, Division of Polymer Chemistry, American Chemical Society.
16. Amsden, B. G. 2006. Biodegradable elastomers and methods of preparing same. US Patent 20030105245
17. Jonsson M, Johansson H O. 2004. Effect of surface grafted polymers on the adsorption of different model proteins. Colloids Surf B Biointerfaces 37: 71-81.
18. Leiva A, Gargallo L, Radic D. 2004. Interfacial properties of poly(caprolactone) and derivatives. Journal of Macromolecular Science—Pure and Applied Chemistry 41 A: 577-583.
19. Satulovsky J, Carignano M A, Szleifer I. 2000. Kinetic and thermodynamic control of protein adsorption. Proc Natl Acad Sci USA 97: 9037-9041.
20. Wildemore J K, Jones D H. 2006. Persistent Granulomatous Inflammatory Response Induced by Injectable Poly-1-lactic Acid for HIV Lipoatrophy. Dermatologic Surgery 32: 1407-1409.
21. Zegzula H D, Buck D C, Brekke J, Wozney J M, Hollinger J O. 1997. Bone formation with use of rhBMP-2 (recombinant human bone morphogenetic protein-2). J Bone Joint Surg Am 79: 1778-1790.
22. Younes, H. M. 2003. New biodegradable elastomers for interferon-gamma delivery. University of Alberta. Doctorate Thesis.
23. Amsden B G, Misra G, Gu F, Younes H M. 2004. Synthesis and characterization of a photo-cross-linked biodegradable elastomer. Biomacromolecules 5: 2479-2486.
24. Takao A, Fusae M, Yu N. 1994. Preparation of cross-linked aliphatic polyester and application to thermo-responsive material. Journal of Controlled Release 32: 87-96.
25. Borzacchiello A, Ambrosio L, Nicolais L, Huang S J. 2000. Synthesis and characterization of saturated and unsaturated poly(alkylene tartrate)s and further cross-linking Journal of Bioactive and Compatible Polymers 15: 60-71.
26. Huang, S. J., Edelman, P. G., and Cameron, J. A. Crosslinkable polyesters for biomedical composites. Polymeric Materials Science and Engineering, Proceedings of the ACS Division of Polymeric Materials: Science and Engineering, Volume 53, Fall Meeting 1985. 53, 515-519. 1985. Chicago, Ill., USA, ACS, Washington, D.C., USA. Polymeric Materials Science and Engineering, Proceedings of the ACS Division of Polymeric Material.
27. Webb, A., Yang, J., and Ameer, G. A novel elastomer for small diameter blood vessel tissue engineering. Transactions—7th World Biomaterials Congress, May 17-21 2004. 1674. 2004. Sydney, Australia, Biomaterials 2004 Congress Managers, Sydney, NSW 2001, Australia. Transactions—7th World Biomaterials Congress.
28. Wang Y, Ameer G A, Sheppard B J, Langer R. 2002. A tough biodegradable elastomer. Nat Biotechnol 20: 602-606.
29. Ameer, A., Yang, J., and Webb, A. 24-3-2005. Novel biodegradable elastomeric scaffold for tissue engineering and light scattering fingerprinting methods for testing the same. U.S. patent Ser. No. 10/945,354
30. Matsuda T, Mizutani M. 2000. Molecular design of photocurable liquid biodegradable copolymers. 2. Synthesis of coumarin-derivatized oligo(methacrylate)s and photocuring. MACROMOLECULES 33: 791-794.
31. Matsuda T, Mizutani M, Arnold S C. 2000. Molecular design of photocurable liquid biodegradable copolymers. 1. Synthesis and photocuring characteristics. Macromolecules 33: 795-800.
32. Hubbell, J. A., Pathak, C. P., Sawhney, A. S., Desai, N. P., and Hill, J. L. 1995. Photopolymerizable biodegradable hydrogels as tissue contacting materials and controlled-release carriers. U.S. Pat. No. 5,410,016.
33. Tipton, A. J., Fujita, A. M. and Dunn, R. L. 1997. Biodegradable Film Dressing and Method for its Formation. U.S. Pat. No. 5,632,727.
34. Gosline J, Lillie M, Carrington E, Guerette P, Ortlepp C, Savage K. 2002. Elastic proteins: biological roles and mechanical properties. Philos Trans R Soc Lond B Biol Sci 357: 121-132.
35. Schliecker G, Schmidt C, Fuchs S, Kissel T. 2004. Characterization and in vitro degradation of poly(2,3-(1, 4-diethyl tartrate)-co-2,3-isopropyliden tartrate). J Control Release 98: 11-23.
36. Decker C. 2001. UV-radiation curing chemistry. Pigm Resin Tech 30: 278-286.
37. K. A. Connors and K. S. Albert. Determination of hydroxy compounds by 4-dimethylaminopyridine-catalyzed acetylation. *J. Pharm. Sci.* 62 (5):845-846, 1973.
38. R. Hill and E. E. Walker. Polymer constitution and fiber properties *J. Polym. Sci.* 3:609, 1948.
39. T. Aoyagi, F. Miyata and Y Nagase. Preparation of cross-linked aliphatic polyester and application in thermo-responsive material, *J. Control Release* 32 (1):87-96, 1994.
40. H. Miyasako, K. Yamamoto, A. Nakao, and T. Aoyagi. Preparation of cross-linked poly[(epsilon-caprolactone)- co-lactide] and biocompatibility studies for tissue engineering materials. *Macromol. Biosci.* 7 (1):76-83, 2007.

41. Jason A. Burdick, Laney M. Philpott, Kristi S. Anseth, Synthesis and characterization of tetrafunctional lactic acid oligomers: A potential in situ forming degradable orthopaedic biomaterial Journal of Polymer Science Part A: Polymer Chemistry 39 (5): 683-692, 2001.

I claim:

1. A thermoset copolymer comprising: polymerizing units of:
    a) about 1 to about 99% by weight of, based on the total mass of the copolymer, a monomer of the formula III:

in which $R^2$ is $C_3$-$C_{20}$ cycloalkylene, $C_1$-$C_{30}$ alkylene, $C_2$-$C_{30}$ alkenylene, or $C_2$-$C_{30}$ alkynylene, said latter 3 groups being straight-chained or branched and/or interrupted by one, two or three $C_3$-$C_{10}$ cyclic moieties therein, and said 4 groups being optionally substituted by one or more groups selected from OH, halo, $OR^4$ and $R^4$, in which $R^4$ is selected from $C_1$-$C_6$ alkyl, $C_2$-$C_6$ alkenyl, $C_2$-$C_6$ alkynyl or $C_3$-$C_6$ cycloalkyl;
    b) about 1 to about 99%, by weight, based on the total mass of the copolymer, of a monomer of the formula V

in which the radical $R^5$ is $C_3$-$C_{20}$ cycloalkylene, $C_1$-$C_{30}$ alkylene, $C_2$-$C_{30}$ alkenylene, $C_2$-$C_{30}$ alkynylene, said latter 3 groups being straight-chained or branched and/or interrupted by one, two or three $C_3$-$C_{10}$ cyclic moieties therein, wherein one or more of the carbon atoms may be replaced by oxygen, and said 4 groups being optionally substituted by one or more groups selected from OH, halo, $OR^4$ and $R^4$, in which $R^4$ is selected from $C_1$-$C_6$ alkyl, $C_2$-$C_6$ alkenyl, $C_2$-$C_6$ alkynyl or $C_3$-$C_6$ cycloalkyl; or $R^5$ is a polyalkylene glycol or a poly-ε-caprolactone; wherein the co-polymer is crosslinked with a photosensitive compound, wherein said copolymer is a thermoset elastomer and an alternating copolymer having the monomer of Formula III alternating with the monomer of Formula V and wherein said copolymer is uniformly biodegradable.

2. The polymer according to claim 1, wherein $R^2$ is $C_3$-$C_{10}$ cycloalkylene, $C_1$-$C_{14}$ alkylene, $C_2$-$C_{10}$ alkenylene, or $C_2$-$C_{10}$ alkynylene, said latter 3 groups being straight-chained or branched and/or interrupted by one, two or three $C_3$-$C_6$ cyclic moieties therein, and said 4 groups being optionally substituted by one to six groups selected from OH, halo, $OR^4$ and $R^4$, in which $R^4$ is selected from $C_1$-$C_6$ alkyl, $C_2$-$C_6$ alkenyl, $C_2$-$C_6$ alkynyl or $C_3$-$C_6$ cycloalkyl.

3. The polymer according to claim 1, wherein the monomer of formula III is selected from

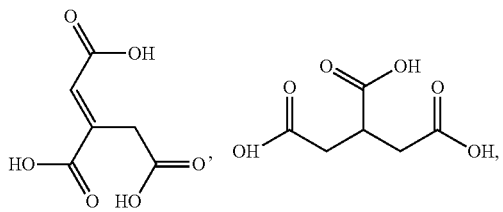

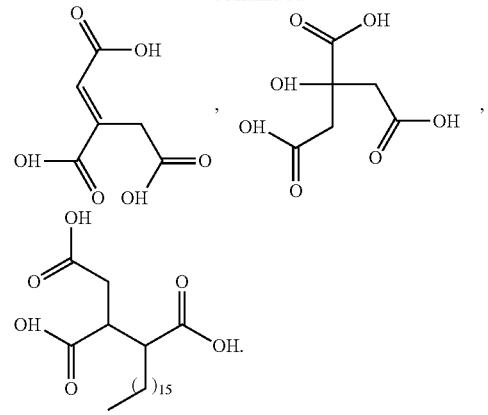

4. The polymer according to claim 3, wherein the monomer of formula III is.

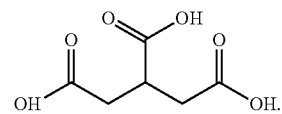 [SMILES: O=C(O)CC(CC(=O)O)C(=O)O]

5. The polymer according to claim 1, wherein $R^5$ is $C_3$-$C_{10}$ cycloalkylene, $C_1$-$C_{10}$-alkylene, $C_2$-$C_{10}$ alkenylene, $C_2$-$C_{10}$ alkynylene, said latter 3 groups being straight-chained or branched and/or interrupted by one, two or three $C_3$-$C_6$ cyclic moieties therein, wherein one or more of the carbon atoms may be replaced by oxygen, and said 4 groups being optionally substituted by one to six groups selected from OH, halo, $OR^4$ and $R^4$, in which $R^4$ is selected from $C_1$-$C_6$ alkyl, $C_2$-$C_6$ alkenyl, $C_2$-$C_6$ alkynyl or $C_3$-$C_6$ cycloalkyl.

6. The polymer according to claim 5, wherein the monomer of formula V is selected from,

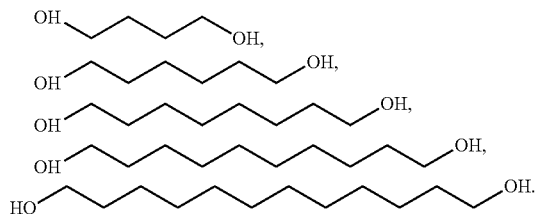

7. The polymer according to claim 5, wherein the monomer of formula V is polyethylene glycol, polypropylene glycol or a poly-ε-caprolactone.

8. The polymer according to claim 7, wherein the monomer of formula V is polyethylene glycol or a poly-ε-caprolactone.

9. The polymer according to claim 7, wherein the polyethylene glycol or poly-ε-caprolactone is PEG 200, PEG 400, PEG 600, PEG 1000, PEG 2000, PEG 6000 or poly-ε-caprolactone diol of molecular weight range 500-2000D.

10. The polymer of claim 1, wherein the copolymer comprises free hydroxyl groups or carboxyl groups which are derivatized with the photosensitive compound.

11. The polymer of claim 10, wherein the photosensitive compound is a UV or visible light photosensitive compound.

12. The polymer of claim 11, wherein the photosensitive compound is selected from

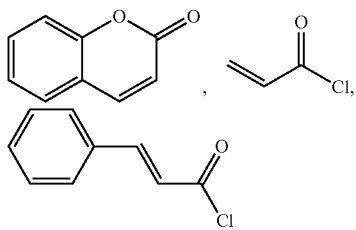

and derivatives thereof.

13. The polymer according to claim 1, wherein the polymer is crosslinked with UV, laser or visible light.

14. The polymer according to claim 1, wherein the polymer is a thermoset elastomer having a glass transition temperature ($T_g$) below 0° C.

15. A process for preparing the thermoset elastomer polymer of claim 1, comprising a reacting monomers of the formula (III) with monomers of the formula (V) to form a condensation co-polymer, wherein the condensation co-polymer is reacted with a photosensitive compound to form a photosensitive condensation polymer which is photocrosslinked to provide the thermoset elastomer polymer.

16. The process according to claim 15, wherein the photosensitive compound is acrolyl chloride or an acrylate derivative, coumarin or a coumarin-derivative, or a cinnamate or a cinnamate derivative.

17. The process according to claim 16, wherein the photosensitive compound is acryloyl chloride.

18. The process according to claim 17, wherein the condensation co-polymer forms an acrylated condensation polymer when reacted with acryloyl chloride.

19. The process according to claim 18, wherein the photosensitive condensation polymer is photocrosslinked upon exposure to UV or visible light having a wavelength of between about 200 to 750 nm.

20. The process according to claim 19, wherein the photosensitive condensation polymer is photocrosslinked upon exposure to visible light having a wavelength of between about 380 to 750 nm.

21. The copolymer according to claim 1, wherein the photosensitive crosslinking compound is capable of reacting to light in the visible region of the electromagnetic spectrum.

* * * * *